United States Patent
Gryzwa et al.

(10) Patent No.: US 11,173,312 B2
(45) Date of Patent: Nov. 16, 2021

(54) INCREASING DYNAMIC RANGE OF STIMULATION CONTROL

(71) Applicant: Medtronic, Inc., Minneapolis, MN (US)

(72) Inventors: Mark Gryzwa, Woodbury, MN (US); Farshad Esnaashari, St. Paul, MN (US); Scott Hawkins, Maple Grove, MN (US); Hector Cantua, Glen Allen, VA (US); Shannon Collins, Xenia, OH (US)

(73) Assignee: Medtronic, Inc., Minneapolis, MN (US)

(*) Notice: Subject to any disclaimer, the term of this patent is extended or adjusted under 35 U.S.C. 154(b) by 288 days.

(21) Appl. No.: 16/368,486

(22) Filed: Mar. 28, 2019

(65) Prior Publication Data

US 2020/0306549 A1    Oct. 1, 2020

(51) Int. Cl.
*A61N 1/36* (2006.01)
*A61N 1/372* (2006.01)
*A61N 1/05* (2006.01)
*A61B 5/00* (2006.01)

(52) U.S. Cl.
CPC .......... *A61N 1/37247* (2013.01); *A61B 5/686* (2013.01); *A61N 1/0551* (2013.01); *A61N 1/3615* (2013.01); *A61N 1/36007* (2013.01); *A61N 1/36071* (2013.01); *A61N 1/36135* (2013.01); *A61N 1/36175* (2013.01); *A61N 1/36192* (2013.01)

(58) Field of Classification Search
CPC .............. A61N 1/37247; A61N 1/0551; A61N 1/3615; A61N 5/686; A61N 1/36071; A61N 1/36135; A61N 1/36192; A61N 1/36175; A61N 1/36007
See application file for complete search history.

(56) References Cited

U.S. PATENT DOCUMENTS

| | | |
|---|---|---|
| 2009/0270947 A1 | 10/2009 | Stone et al. |
| 2016/0022989 A1 | 1/2016 | Pfeifer |
| 2016/0129259 A1* | 5/2016 | Libbus ............... A61N 1/37235 607/59 |
| 2017/0319856 A1 | 11/2017 | Moffitt et al. |
| 2018/0001023 A1 | 1/2018 | Gerber et al. |
| 2018/0050207 A1 | 2/2018 | Hamann et al. |

* cited by examiner

*Primary Examiner* — Rex R Holmes
(74) *Attorney, Agent, or Firm* — Shumaker & Sieffert, P.A.

(57) ABSTRACT

Techniques for configuring electrical stimulation therapy parameters is described. Based on user input, processing circuitry may keep a first therapy parameter substantially constant and increase a value of a second therapy parameter until increasing the second therapy parameter further causes the second therapy parameter to be bigger than threshold value. The processing circuitry may adjust the second therapy parameter value and adjust the first therapy parameter value. Prior to adjustment, the first and second therapy parameters set a first intensity, and after adjustment, the first and second therapy parameters set a second intensity that is greater than or equal to the first intensity. The processing circuitry causes delivery of therapy at the second intensity.

34 Claims, 15 Drawing Sheets

INCREASING DYNAMIC RANGE OF STIMULATION CONTROL

TECHNICAL FIELD

The disclosure relates to medical devices and, more particularly, to configuration of electrical stimulation therapy parameters.

BACKGROUND

Medical devices may be external or implanted and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patent. For bipolar stimulation, the electrodes used for stimulation may be on one or more leads. For unipolar stimulation, the electrodes may be on one or more leads and an electrode on a stimulator housing located remotely from the target site (e.g., near the clavicle, lower back or another implant site). It may be possible to use leadless stimulation using electrodes mounted on the stimulation housing. Electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as stimulation parameters. A set of parameters, such as a set including electrode combination, electrode polarity, amplitude, pulse width, and pulse rate, may be referred to as a program in the sense that they define the electrical stimulation therapy to be delivered to the patient.

SUMMARY

In general, techniques for configuring electrical stimulation therapy by utilizing one or more stimulation therapy intensity values are described. The stimulation therapy intensity value is indicative of the energy delivered by a medical device, and is based on pulse amplitude, pulse width, and frequency. A user enters a stimulation therapy intensity value, and a medical device may determine the appropriate pulse width, pulse amplitude, and/or frequency that achieves the stimulation therapy intensity value. The user subsequently updates the stimulation therapy intensity value, and in response, the medical device may keep one or more parameters (e.g., pulse width, pulse amplitude, or frequency) substantially constant, including constant, and only change one of the parameters to achieve the updated stimulation therapy intensity value. As the user keeps updating the stimulation therapy intensity value, it is possible that the parameter being changed increases beyond a threshold value. In this case, the medical device may increase one or the one or more parameters that were kept substantially constant, allowing the medical device to set the value of the parameter previously being changed to a value less than the threshold to achieve the desired stimulation therapy intensity value.

The example techniques may provide technical solutions to technical problems and provide a practical application of the technical solutions. For instance, the user may need to input a stimulation therapy intensity value rather than separately input pulse width, pulse amplitude, and frequency. This way, there is only one parameter for the user to adjust (e.g., user-adjusted parameter), promoting ease of use. However, where there is only one user-adjusted parameter for the user to adjust, the therapy still includes at least three parameters (e.g., three device-adjusted parameters): pulse width, pulse amplitude, and frequency. Accordingly, with control of only one user-adjusted parameter, there may be a possibility to increase a value of a device-adjusted parameter (e.g., pulse width, pulse amplitude, or frequency) above a threshold. Limiting the value of a device-adjusted parameter, without further changes, may be insufficient because the stimulation therapy intensity is unnecessarily limited to a level below the desired stimulation therapy intensity. By limiting the values at which the device-adjusted parameters (e.g., pulse width, pulse amplitude, or frequency) can be set, and also automatically adjusting other device-adjusted parameters to achieve the desired stimulation therapy intensity, the techniques described in this disclosure may promote better operation of medical devices to provide efficacious therapy.

In one example, the disclosure describes a method comprising responsive to each of a plurality of user input entries to increase electrical stimulation therapy intensity, holding a value of a first therapy parameter substantially constant and increasing a value of a second therapy parameter, responsive to receiving a user input entry to increase electrical stimulation therapy intensity that causes a present value of the second therapy parameter to be at or greater than a threshold value for the second therapy parameter, adjusting the present value of the second therapy parameter from a first value of the second therapy parameter to a second value of the second therapy parameter, and adjusting a present value of the first therapy parameter from a first value of the first therapy parameter to a second value of the first therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity, and causing delivery of therapy at the second intensity.

In one example, the disclosure describes a system comprising a memory configured to store one or more threshold values for one or more therapy parameters and processing circuit. The processing circuitry is configured to responsive to each of a plurality of user input entries to increase electrical stimulation therapy intensity, hold a value of a first therapy parameter substantially constant and increase a value of a second therapy parameter, responsive to receiving a user input entry to increase electrical stimulation therapy intensity that causes a present value of the second therapy parameter to be at or greater than a threshold value stored in memory for the second therapy parameter, adjust the present value of the second therapy parameter from a first value of the second therapy parameter to a second value of the second therapy parameter, and adjust a present value of the first therapy parameter from a first value of the first therapy parameter to a second value of the first therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity, and cause delivery of therapy at the second intensity.

In another example, the disclosure describes a computer-readable storage medium comprising instructions to cause a programmable processor to responsive to each of a plurality of user input entries to increase electrical stimulation therapy intensity, hold a value of a first therapy parameter substantially constant and increasing a value of a second therapy parameter, responsive to receiving a user input entry to increase electrical stimulation therapy intensity that causes a present value of the second therapy parameter to be at or greater than a threshold value for the second therapy parameter, adjust the present value of the second therapy parameter from a first value of the second therapy parameter to a second value of the second therapy parameter, and adjust a present value of the first therapy parameter from a first value of the first therapy parameter to a second value of the first therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity, and cause delivery of therapy at the second intensity.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
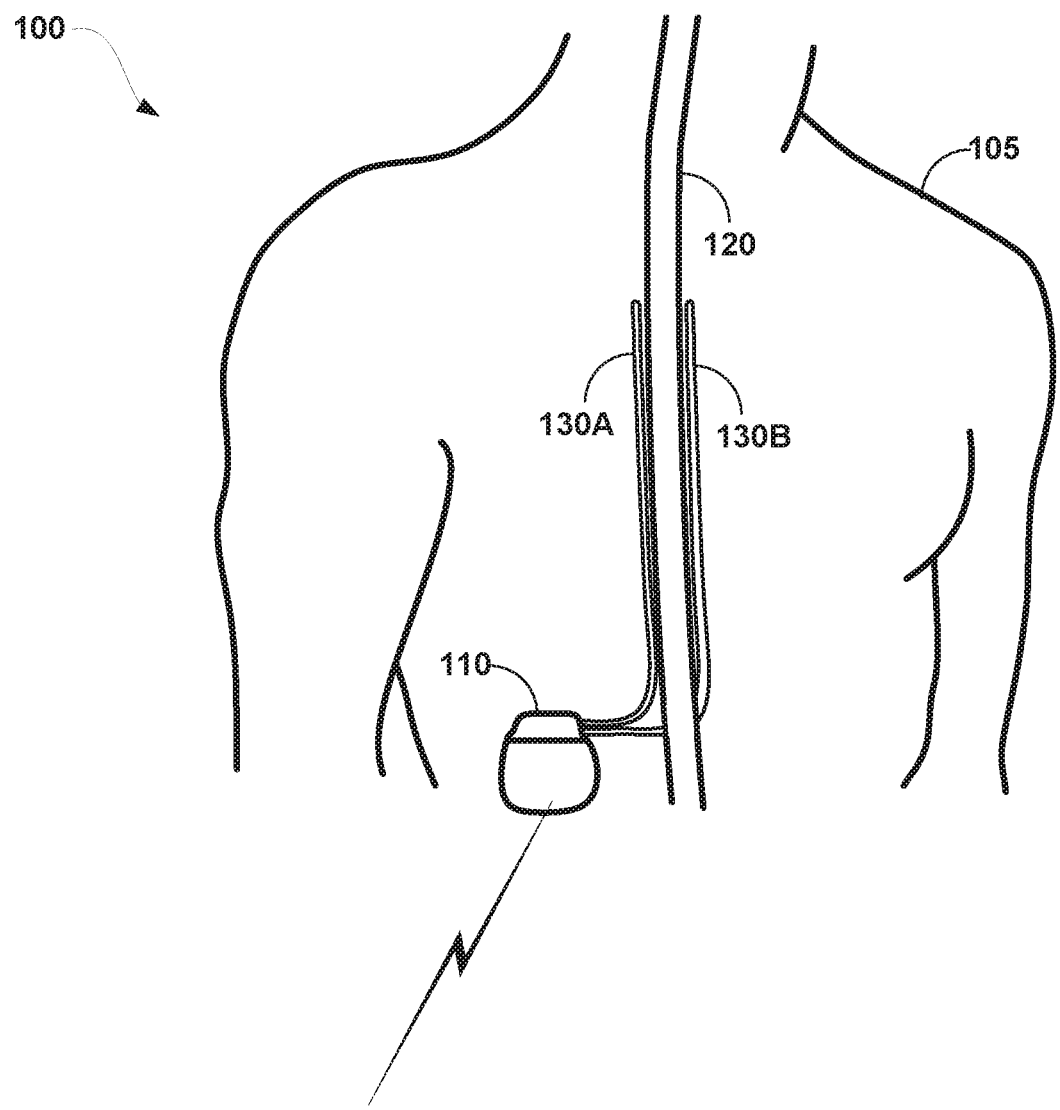
FIG. 1 is a conceptual diagram illustrating an example system that includes an implantable medical device (IMD) configured to deliver therapy to a patient according to an example of the techniques of the disclosure.

Electrical stimulation therapy may provide relief to a patient from many conditions. However, the stimulation therapy efficacy is contingent on a clinician or other user correctly configuring, or programming, the stimulation parameters in a manner that provides appropriate therapy to the patient while minimizing side-effects produced from the stimulation. Due to a number of factors, including physiological diversity, patient condition (e.g., disease or disorder) differences, and inaccuracies or changes in stimulation lead placement, the parameters may vary greatly between patients. Therefore, typically a clinician individually programs stimulation parameters for each patient. This programming process may continue throughout the therapy as patient needs change.

This disclosure generally relates to techniques for controlling multiple therapy parameters with a single user input. Currently, users (e.g., patients and clinicians) can control multiple parameters when setting therapy. For instance, users can control amplitude, pulse width, and frequency of the electrical stimulation therapy. However, the efficacy of therapy may be based more on the energy delivered by the stimulation therapy (e.g., stimulation therapy intensity), resulting from a combination of these parameters, than on any one of these parameters individually.

As an example, the energy delivered in any therapy pulse may be based on the amplitude, pulse width, and frequency. Accordingly, if the amplitude is doubled, and pulse width is halved, or the amplitude is halved, and the pulse width is doubled, the efficacy of the therapy in terms of the amount of energy delivered may remain substantially the same if there is no change to the frequency.

Users may find it cumbersome to modify each parameter individually to identify therapy parameters that provide effective therapy. Moreover, in setting therapy parameters, there may be times when a user reaches a maximum value (e.g., maximum allowed or maximum possible) for a first parameter and is forced to modify a value of a second parameter. In some examples, after modifying the second parameter, the user may need to start adjusting the first parameter but starting from a base value of the first parameter. Such iterative processes for therapy parameter setting may cause users to set therapy parameters at less than ideal values due to the relatively long amount of time needed to set the parameters to values that provide higher efficacy.

In accordance with one or more example techniques, a programmer may provide one input, e.g., a single input, that a user can use to control the electrical stimulation therapy intensity rather than requiring the user to select levels for a plurality of the parameters (e.g., separately select levels for the amplitude, frequency, and pulse width). In such an example, the user may increase (or decrease) the intensity of the electrical stimulation therapy, and the programmer may keep most (including all) parameters, substantially constant and change one of the therapy parameters. For example, to achieve a desired intensity, a programmer or other control unit may adjust a value of a single one of amplitude, frequency, pulse width while keeping the other two parameter values substantially constant.

Keeping parameter values substantially constant may mean that while there may be some minor changes in the parameter values being kept substantially constant, the changes in the parameter values should not be of such degree that there is substantial change to the desired intensity level (e.g., less than 1%, 5%, 10%, or 15% different than the desired intensity level). That is, to keep a parameter value substantially constant may mean that the parameter value is allowed to within a range that ensures that the desired intensity level does not change by more than 1%, 5%, 10%, or 15% as a few examples. In some examples, keeping parameter values substantially constant means that the desired intensity level does not shift to a point where the patient experiences a different amount of therapy efficacy. In some examples, keeping parameter values substantially constant may mean that the parameter values are kept within a range of 1%, 5%, 10%, or 15% from previous values. In some examples, keeping parameter values substantially constant includes cases where the parameter values are kept constant.

However, if a request to increase the electrical stimulation therapy intensity (e.g., user-adjusted parameter) would cause the device-adjusted parameter (e.g., one of amplitude, frequency, pulse width) that is being modified to become greater than a threshold value, the programmer may automatically reduce the parameter being modified and adjust one or more of the other parameters previously being kept substantially constant so that the resulting electrical stimulation therapy intensity is at the desired level or at the level the electrical stimulation therapy intensity was at before the request to increase (or at a maximum permitted level that is an increase but not an increase about the maximum permitted level). There may be technical benefits in reducing the parameter being modified. For instance, by reducing the parameter being modified, for subsequent entries to increase the electrical stimulation therapy intensity, it may be possible to go back to increasing the parameter that is was being modified. For instance, the amplitude may reach its threshold level, and the amplitude is reduced and the pulse width is increased to achieve the desired therapy intensity. Then, it may be possible to increase to go back to increasing the amplitude for subsequent entries to increase the therapy intensity.

In one or more examples, for power reasons and patient comfort, it may be undesirable to keep a therapy parameter at its threshold level and deliver therapy where one of the therapy parameters is at its threshold level. The patient may feel discomfort in such cases, and there is a tendency for the battery to drain faster as well.

In these cases, because the therapy parameter that was being modified is reduced, the therapy parameter is now less than the threshold value and can be increased further. Also, because the other therapy parameters are automatically modified to accommodate further increases in the therapy parameter that had reached the threshold value, the user does not need to separately modify the therapy parameters. In this way, the example techniques provide a practical application of providing a seamless way in which the user can control the electrical stimulation therapy intensity without needing to separately select each therapy parameter.

As an example to assist with understanding, assume that the frequency is 1 kHz, the pulse width is 90 micro-seconds, and the amplitude is currently at 0 mA. In this example, the user may increase the stimulation therapy intensity, and the programmer may increase the amplitude (e.g., in 0.2 mA steps) but keep the frequency and pulse width substantially constant. The programmer may then cause an implantable medical device (IMD) of the patient to deliver therapy based on the therapy parameters. The user may keep increasing the stimulation therapy intensity, and the programmer may keep increasing the amplitude and causing the IMD to deliver at the increased amplitude.

The programmer may receive a request to increase the stimulation therapy intensity but doing so would cause the amplitude to be greater than a threshold amplitude of 20 mA. In this example, the programmer may half the amplitude to be 10 mA but double the pulse width to be 180 microseconds and keep the frequency the same. The programmer may keep the frequency the same at 1 kHz. In this way, the energy being delivered (e.g., stimulation therapy intensity) is the same but is produced by a different combination of therapy parameter settings.

Responsive to the user increasing the stimulation therapy intensity, the programmer may again increase the amplitude, and in some examples, at half the original rate (e.g., at 0.1 mA steps instead of 0.2 mA steps) to maintain a linear energy output. For instance, because the pulse width doubled, the steps of the amplitude are halved so that the patient experiences the same linear increase in the overall stimulation therapy intensity rather than experiencing a faster rising stimulation therapy intensity for each request to increase the stimulation therapy intensity.

FIG. 1 is a conceptual diagram illustrating example system 100 that includes implantable medical device (IMD) 110 configured to deliver electrical stimulation therapy to patient 105. In the example shown in FIG. 1, IMD 110 is configured to deliver spinal cord stimulation (SCS) therapy according to the techniques of the disclosure. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 may be selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameters of a therapy stimulation program that define the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, or pulse shape of stimulation delivered by the electrodes. However, as described in more detail, a user may be permitted to enter only an electrical stimulation intensity value, rather than separately entering each of the therapy parameters. These stimulation parameters of therapy pulses are typically predetermined parameter values determined prior to delivery of the therapy pulses. However, in some examples, system 100 may change one or more parameter values automatically based on one or more factors or based on user input.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of spinal cord stimulation (SCS), deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 may include one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

In one or more examples, while the therapy stimulation program may define values for voltage or current pulse amplitude, pulse width, and pulse rate for stimulation pulses delivered by IMD 110, as described in more detail below, it may be possible for a user to enter only an electrical stimulation therapy intensity value (e.g., via programmer 150). IMD 110 (or programmer 150) may then determine the therapy parameter values based on the electrical stimulation therapy intensity values entered by the user, which reduces the number of inputs the user needs to adjust, allowing for quicker and more accurate selection of the correct therapy parameters. Quicker and more accurate selection of the correct therapy parameters results in more efficacious therapy and thereby improves the overall operation of system 100.

A user, such as a clinician or patient 105, may interact with a user interface of an external programmer 150 to program IMD 110. As one example, external programmer 150 may receive the electrical stimulation therapy intensity as a user input entry and determine the therapy parameters (e.g., amplitude, pulse width, and frequency) to achieve the user input entry of the electrical stimulation therapy intensity, including whether the electrical stimulation therapy intensity would cause therapy a parameter to be greater than a threshold, and to adjust the parameters accordingly. External programmer 150 may output the parameters to IMD 110 as part of programming IMD 110.

In some examples, external programmer 150, as part of programming, may output to IMD 110 information indicative of the user input entry of the electrical stimulation therapy intensity. In such examples, IMD 110 may determine the therapy parameters (e.g., amplitude, pulse width, and frequency) to achieve the user input entry of the electrical stimulation therapy intensity, including whether the electrical stimulation therapy intensity would cause therapy a parameter to be greater than a threshold, and to adjust the parameters accordingly.

Programming of IMD 110 may refer generally to the generation and transfer of commands, programs, or other information to control the operation of IMD 110. In this manner, IMD 110 may receive the transferred commands and programs from programmer 150 to control electrical stimulation therapy (e.g., therapy pulses). For example, external programmer 150 may transmit therapy stimulation programs, stimulation parameter adjustments, therapy stimulation program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and programmer 150 may communicate via wireless communication using any techniques known in the art. Examples of communication techniques may include, for example, radiofrequency (RF) telemetry and inductive coupling, but other techniques are also contemplated. In some examples, programmer 150 may include a communication head that may be placed proximate to the patient's body near the IMD 110 implant site to improve the quality or security of communication between IMD 110 and programmer 150. Communication between programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 may modify therapy stimulation programs as therapy needs of patient 105 evolve over time. For example, the modification of the therapy stimulation programs may cause the adjustment of at least one parameter of the plurality of therapy pulses.

As described, a user (e.g., patient 105 or a clinician) use programmer 150 to set the therapy parameters used for delivering stimulation therapy. One way to set the therapy parameters is to have the user manually adjust multiple therapy parameters at the same time, and after each adjustment, programmer 150 may output the therapy parameters to IMD 110 and IMD 110 may deliver therapy according to the therapy parameters. If patient 105 does not experience efficacious treatment, the user may again adjust multiple therapy parameters, and the process may repeat until patient 105 experiences efficacious treatment. However, the user may find that adjusting multiple therapy parameters at the same time to find efficacious treatment is cumbersome because there are at least three different variable (e.g., amplitude, pulse width, and pulse frequency (pulse rate)) that need to be adjusted. In such cases, due to the burden of needing to adjust multiple parameters, the user may select therapy parameters that may not provide the most efficacious treatment by giving up or by not finding the ideal combination of therapy parameters.

To address this, it may be possible to present the user with options to control all therapy parameters, but the user only adjusts one therapy parameter at a time. For instance, the user is presented with an initial amplitude, pulse width, and pulse frequency. The user then increases one of the therapy parameters (e.g., amplitude) and keeps the other parameters substantially constant. Similar to above, programmer 150 outputs the therapy parameters to IMD 110 and IMD 110 delivers therapy based on the parameters. This process repeats until patient 105 experiences efficacious treatment.

However, there are threshold levels for each of the parameters that the parameters cannot exceed. It may be possible that the user in increasing one parameter ends up reaching the threshold for that parameter without experiencing sufficiently efficacious treatment. In this case, the user may then start to increase other therapy parameters (e.g., pulse width) and keep the amplitude at the threshold level. In one or more examples, for power reasons and patient comfort, it may be undesirable to keep a therapy parameter at its threshold level and have IMD 110 deliver therapy where one of the therapy parameters is at its threshold level.

Therefore, in some examples, after reaching a threshold level for a parameter, programmer 150 may automatically reduce the value of the parameter that reached the threshold level. The user may then adjust another therapy parameter until patient 105 experiences efficacious treatment. Even under this case, the user may find the process burdensome because after reaching the threshold level for a parameter, the user is back to needing to control multiple therapy parameters at the same time.

In one or more examples, this disclosure describes techniques that allow a user to control therapy parameters by controlling a stimulation therapy intensity value rather than controlling a plurality of therapy parameters separately. It should be understood that there is a possibility that the user can separately control the therapy parameters. In other words, techniques described in this disclosure that allow the user to control a plurality of therapy parameters by controlling a stimulation therapy intensity value should not be considered as limiting the example techniques to exclude having separate control of at least some of the therapy parameters. For example, programmer 150 may include buttons that allow the user to separately control the different therapy parameters. In some examples, programmer 150 or IMD 110 may determine the therapy parameters based on electrical stimulation therapy intensity, and the user may after the initial determination of the therapy parameters, provide fine tuning by separately controlling the therapy parameters.

In general, the efficacy of therapy is a function of energy delivered by the therapy. For instance, patient 105 feels the intensity of the therapy, which is a measure of the energy delivered by the therapy. For example, the higher the energy that is delivered, up to a certain point that is different for different patients, the more paresthesia or suppression of pain patient 105 may experience. After the certain point of energy, patient 105 may experience discomfort.

The stimulation therapy intensity is a factor of the amplitude, pulse width, and pulse frequency (e.g., pulse rate). For instance, the stimulation therapy intensity is directly correlated to the multiplication of the amplitude, pulse width, and pulse frequency. In some examples, programmer 150 may display a stimulation therapy intensity value, and the user may increase or decrease the stimulation therapy intensity value. In this disclosure, the display of the stimulation therapy intensity value should not be considered limited to examples where the stimulation therapy intensity value that is displayed represents the actual energy of the stimulation therapy. For instance, the user may be able to increase or decrease the stimulation therapy intensity value between a value of 0 to 10. Each of these values may correspond to a specific amount of stimulation therapy intensity (e.g., specific amount of energy in the stimulation therapy), but from the perspective of the user, it may not be of consequence whether the user sees a generic unit-less number (e.g., 0 to 10) or a specific number of the amount of energy (e.g., in Joules).

In one or more examples, programmer 150 may initially set the therapy parameters (e.g., amplitude is 0 mA, pulse width 90 micro-seconds, and pulse frequency 1 kHz). Then, in response to a request to increase the stimulation therapy intensity (e.g., from the user), programmer 150 may increase a first therapy parameter (e.g., increase amplitude by 0.2 mA increments) but keep a second therapy parameter (e.g., pulse width and/or pulse frequency) substantially constant.

As described above, keeping parameter values substantially constant may mean that while there may be some minor changes in the parameter values being kept substantially constant, the changes in the parameter values should not be of such degree that there is substantial change to the desired intensity level (e.g., less than 1%, 5%, 10%, or 15% different than the desired therapy intensity level). That is, to keep a parameter value substantially constant may mean that the parameter value is allowed to within a range that ensures that the desired intensity level does not change by more than 1%, 5%, 10%, or 15% as a few examples. For example, if in response to the user input, the stimulation therapy intensity is to be X, then, while there may be some changes in the therapy parameter values being kept constant, the changes should be such that the actual stimulation therapy intensity is not more than 1%, 5%, 10%, or 15% different than X. In some examples, keeping parameter values substantially constant means that the desired intensity level does not shift to a point where the patient experiences a different amount of therapy efficacy. In some examples, keeping parameter values substantially constant may mean that the parameter values are kept within a range of 1%, 5%, 10%, or 15% from previous values. In some examples, keeping parameter values substantially constant includes cases where the parameter values are kept constant.

Like above, programmer 150 may cause IMD 110 to deliver the therapy based on the therapy parameters and may keep increasing the first therapy parameter until the first therapy parameter reaches its threshold or patient 105 indicates efficacious therapy. In the case of efficacious therapy, IMD 110 may then deliver therapy based on the therapy parameters.

However, in case that the first therapy parameter reaches the threshold value or exceeds the threshold, programmer 150 may simultaneously reduce the value of the first therapy parameter (e.g., for potential patient comfort and power efficiency) and increase the value of the second therapy parameter such that the stimulation therapy intensity remains the same or is increased to the desired level and with the therapy parameters being less than their respective threshold values. As an example, assume that the threshold value for the amplitude is 20 mA, and the pulse width is 90 micro-seconds and the pulse frequency is 1 kHz. In this example, if, during the increases in the stimulation therapy intensity, the user reaches the 20 mA threshold for the amplitude, programmer 150 may reduce the current from 20 mA to 10 mA (as one example) and increase the pulse width from 90 micro-seconds to 180 micro-seconds. In this example, the relationship is described as being linear (e.g., 100% increase in the pulse width is proportional to a 50% decrease in amplitude) but the example techniques are not so limited. The pulse frequency may remain the same. In this case, because the amplitude is halved and the pulse width is doubled, with the pulse frequency remaining the same, the energy delivered by IMD 110 (e.g., the stimulation therapy intensity) is the same.

In the above example, when the amplitude reached the threshold value of 20 mA, programmer 150 reduced the amplitude and increased the pulse width. However, in some examples, when the amplitude is increased form the threshold value of 20 mA, programmer 150 may reduce the amplitude and increase the pulse width. For instance, if the amplitude is at 20 mA and steps to increase the current are 0.2 mA, and there is an increase in the stimulation therapy intensity, programmer 150 may (assuming no threshold) increase the current to 20.2 mA. After determining that the increase in the stimulation therapy intensity would cause the current to go above the threshold, programmer 150 may automatically reduce the current to 10.1 mA, and double the pulse width to 180 micro-seconds so that the stimulation therapy intensity is set to the desired stimulation therapy intensity.

In some examples, after reducing the amplitude of the current, the user may keep increasing the stimulation therapy intensity, and in response, programmer 150 may increase the amplitude of the current. However, to keep a linear increase in the stimulation therapy intensity, programmer 150 may decrease the step size in the increase of the amplitude so the rate of increase in the stimulation therapy intensity is kept substantially constant. For example, when the step size of the change in amplitude is 0.2 mA and the pulse width is 90 micro-seconds, the amount of increase in the stimulation therapy intensity for each request to increase the stimulation therapy intensity is correlated approximately to (0.2 mA)*(90 micro-seconds). Then, when the pulse width is increase to 180 micro-seconds, to keep the amount of increase in the stimulation therapy intensity substantially constant, the step size of the amount by which the current is adjusted needs to be lowered to 0.1 mA because (0.2 mA)*(90 micro-seconds) equals (0.1 mA)*(180 micro-seconds). Accordingly, after the pulse width is increased to 180 micro-seconds, programmer 150 may increase the amplitude in steps of 0.1 mA so that the rate of increase in the stimulation therapy intensity is substantially constant, resulting in a linear increase in the stimulation therapy intensity.

In the above examples, programmer 150 adjusts the amplitude and keeps the pulse width and pulse frequency substantially constant. However, the example techniques are not so limited, and programmer 150 may adjust any of the parameters and keep one or more of the other parameters substantially constant. Also, when a therapy parameter reaches its threshold, the therapy parameter that reaches its threshold may be reduced, and any of the other parameters may be increased. In some examples, only one other parameter may be increased, and in some examples, two or more of the other parameters may be increased or one or some may be increased and another or the other decreased.

Moreover, the above example techniques are described with respect to programmer 150. However, the example techniques are not so limited. In some examples, programmer 150 may output information to IMD 110 that indicates that the user is increasing the stimulation therapy intensity. In response, IMD 110 may increase a parameter until the parameter reaches the threshold or becomes greater than the threshold. IMD 110 may then decrease the parameter that reached the threshold and increase another parameter to keep the stimulation therapy intensity substantially constant or at the desired level.

The above examples are described with respect to increasing the stimulation therapy intensity. The example techniques may be applied in the inverse when stimulation therapy intensity is being decreased. For instance, there may be a lower threshold (e.g., 0.2 mA), and when programmer 150 or IMD 110 reaches the lower threshold of a therapy parameter, programmer 150 or IMD 110 may increase the therapy parameter that reached the lower threshold and increase another parameter to keep the stimulation therapy intensity substantially constant (e.g., less than 1%, 5%, 10%, or 15% different than the stimulation therapy intensity) or at the desired level.

In this way, a medical device (e.g., programmer 150 or IMD 110) may be configured to perform one or more example techniques described in this disclosure. For example, the medical device may be configured to be responsive to each of a plurality of entries to increase electrical stimulation therapy intensity, hold a value of a first therapy parameter substantially constant and increase a value of a second therapy parameter. Responsive to receiving an entry to increase electrical stimulation therapy intensity that causes a present value of the second therapy parameter to be at or greater than a threshold value for the second therapy parameter, the medical device may be configured to adjust the present value of the second therapy parameter from a first value of the second therapy parameter to a second value of the second therapy parameter, and adjust a present value of the first therapy parameter from a first value of the first therapy parameter to a second value of the first therapy parameter. The first value of the first therapy parameter and the first value of the second therapy parameter set a first intensity and the second value of the first therapy parameter and the second value of the second therapy parameter set a second intensity, and the second intensity is greater than or equal to the first intensity. The medical device may be configured to cause delivery of therapy at the second intensity value.

In some examples, responsive to each of a plurality of user input entries to increase electrical stimulation therapy intensity, it may be possible for the medical device to simultaneously change multiple therapy parameters. For example, the medical device may change a value of a first therapy parameter by a little so that the first therapy parameter is held to a value that is substantially constant and increase a value of a second therapy parameter. As another example, the medical device may change a value of the first therapy parameter and change a value of the second therapy parameter.

Then, responsive to receiving a user input entry to increase electrical stimulation therapy intensity that causes a present value of the second therapy parameter to be at or greater than a threshold value for the second therapy parameter, the medical device may adjust the present value of the second therapy parameter from a first value of the second therapy parameter to a second value of the second therapy parameter, and adjust a present value of the first therapy parameter from a first value of the first therapy parameter to a second value of the first therapy parameter. As above, the first value of the first therapy parameter and the first value of the second therapy parameter set a first intensity and the second value of the first therapy parameter and the second value of the second therapy parameter set a second intensity, and the second intensity is greater than or equal to the first intensity. The medical device may then cause delivery of therapy at the second intensity.

Accordingly, the example techniques described in this disclosure should not be considered limited to examples where one or more therapy parameter are kept substantially constant. The example techniques may perform in a similar manner in examples where therapy parameters are not kept constant or where two or more therapy parameters are adjusted (e.g., increased or decreased) responsive to a user input entry to increase therapy intensity. In such examples, when the increase in a therapy parameter would cause the therapy parameter to be greater than a threshold value, the medical device may adjust the therapy parameters to ensure that the therapy parameters are not above the respective therapy threshold values.

For ease, the example techniques are described with respect to keeping a therapy parameter constant and increasing or decreasing only one therapy parameter responsive to each of a plurality of user input entries to increase or decrease electrical stimulation therapy intensity. However, the techniques described in this disclosure should not be considered limited to such examples. For instance, for ease, the example techniques are described where, responsive to each of a plurality of user input entries to increase electrical stimulation therapy intensity, a medical device holds a value of a first therapy parameter substantially constant and increases a value of a second therapy parameter. However, in some examples, the medical device may change both the first and second therapy parameters.

Figure 2:
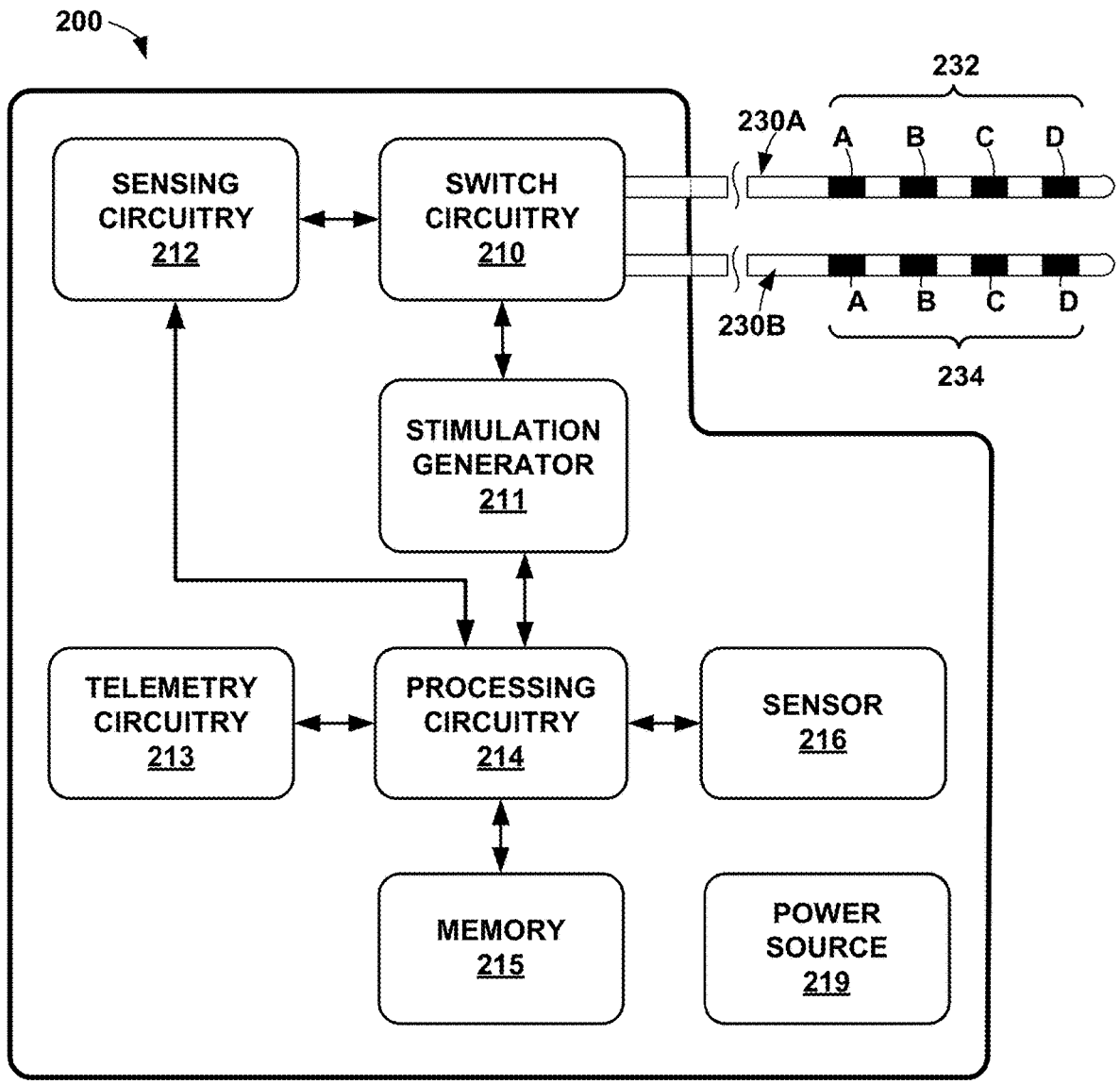
FIG. 2 is a block diagram of the example IMD of FIG. 1 for delivering therapy according to an example of the techniques of the disclosure.

FIG. 2 is a block diagram of IMD 200. IMD 200 may be an example of IMD 110 of FIG. 1. In the example shown in FIG. 2, IMD 200 includes processing circuitry 214, memory 215, stimulation generator 211, sensing circuitry 212, telemetry circuitry 213, sensor 216, and power source 219. Each of these circuits may be or include programmable or fixed function circuitry configured to perform the functions attributed to respective circuitry. For example, processing circuitry 214 may include fixed-function or programmable circuitry, stimulation generator 211 may include circuitry configured to generate stimulation signals such as pulses or continuous waveforms on one or more channels, sensing circuitry 212 may include sensing circuitry for sensing signals, and telemetry circuitry 213 may include telemetry circuitry for transmission and reception of signals. Memory 215 may store computer-readable instructions that, when executed by processing circuitry 214, cause IMD 200 to perform various functions. Memory 215 may be a storage device or other non-transitory medium.

Memory 215 may be configured to store threshold values for the different therapy parameters. For instance, memory 215 may store a maximum and minimum threshold values for the amplitude, the pulse width, and the pulse frequency. Processing circuitry 214 may compare the threshold values to the present values of the therapy parameters to determine whether to reduce or increase the level of one therapy parameter that is at a threshold and increase or reduce the level of another therapy parameter to keep the stimulation therapy intensity at the desired level.

In addition, memory 215 may store therapy stimulation programs. Each stored therapy stimulation program defines values for a set of electrical stimulation parameters (e.g., a therapy parameter set), such as a stimulation electrode combination, electrode polarity, current or voltage amplitude, pulse width, pulse rate, and pulse shape. Processing circuitry 214, either based on its own calculations or based on information received from programmer 150, may adjust the therapy parameters in accordance with the techniques described in this disclosure.

Accordingly, in some examples, stimulation generator 211 generates electrical stimulation signals in accordance with the electrical stimulation parameters noted above. Other ranges of therapy parameter values may also be useful and may depend on the target stimulation site within patient 105. While stimulation pulses are described, stimulation signals may be of any form, such as continuous-time signals (e.g., sine waves) or the like. Switch circuitry 210 may include one or more switch arrays, one or more multiplexers, one or more switches (e.g., a switch matrix or other collection of switches), or other electrical circuitry configured to direct stimulation signals from stimulation generator 211 to one or more of electrodes 232, 234, or directed sensed signals from one or more of electrodes 232, 234 to sensing circuitry 212. In other examples, stimulation generator 211 and/or sensing circuitry 212 may include sensing circuitry to direct signals to and/or from one or more of electrodes 232, 234, which may or may not also include switch circuitry 210.

Processing circuitry 214 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 214 herein may be embodied as firmware, hardware, software or any combination thereof. Processing circuitry 214 controls stimulation generator 211 to generate stimulation signals according to the therapy parameters to apply stimulation parameter values such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 214 also controls stimulation generator 211 to generate and apply the stimulation signals to selected combinations of electrodes 232, 234. In some examples, stimulation generator 211 includes a switch circuit (instead of, or in addition to, switch circuitry 210) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generator 211 does not include a switch circuit and switch circuitry 212 does not interface between stimulation generator 211 and electrodes 232, 234. In these examples, stimulation generator 211 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated positive voltage source and regulated negative voltage source or regulated current source and regulated current sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter or circumference of the lead at each of the locations A, B, C, and D. In one example, the electrodes may be electrically coupled to stimulation generator 211, e.g., via switch circuitry 210 and/or switching circuitry of the stimulation generator 211, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 212 is incorporated into a common housing with stimulation generator 211 and processing circuitry 214 in FIG. 2, in other examples, sensing circuitry 212 may be in a separate housing from IMD 200 and may communicate with processing circuitry 214 via wired or wireless communication techniques.

Sensor 216 may include one or more sensing elements that sense values of a respective patient parameter. Sensor 216 may include one or more accelerometers, optical sensors, chemical sensors, temperature sensors, pressure sensors, or any other types of sensors. Sensor 216 may output patient parameter values that may be used as feedback to control delivery of therapy. For example, sensor 216 may indicate patient activity, and processing circuitry 214 may select appropriate therapy program from memory 215 based on the indicated patient activity.

Telemetry circuitry 213 supports wireless communication between IMD 200 and an external programmer 150 (not shown in FIG. 2) or another computing device under the control of processing circuitry 214. Processing circuitry 214 of IMD 200 may receive, as updates to programs, values for various stimulation parameters such as amplitude and electrode combination, from the external programmer 150 via telemetry circuitry 213. Telemetry circuitry 213 in IMD 200, as well as telemetry circuits in other devices and systems described herein, such as the external programmer, may accomplish communication by radiofrequency (RF) communication techniques. In addition, telemetry circuitry 213 may communicate with an external medical device programmer (not shown in FIG. 2) via proximal inductive interaction of IMD 200 with the external programmer 150. Accordingly, telemetry circuitry 213 may send information to the external programmer 150 on a continuous basis, at periodic intervals, or upon request from IMD 110 or the external programmer 150.

Power source 219 delivers operating power to various components of IMD 200. Power source 219 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used.

According to the techniques of the disclosure, a user may be able to adjust therapy parameters by adjusting an electrical stimulation therapy intensity, rather than adjusting each individual therapy parameter. However, as described above, in such example techniques it is possible that a therapy parameter will reach its threshold value, which can complicate the adjustment. This disclosure describes example techniques to address such issues.

In some examples, processing circuitry 214 may be configured to perform example operations or may be configured to perform the example operations together with circuitry of programmer 150. For ease, the following is described with respect to processing circuitry 214.

For example, responsive to each of a plurality of entries to increase electrical stimulation therapy intensity, processing circuitry 214 may be configured to hold a value of a first therapy parameter substantially constant and increase a value of a second therapy parameter. Responsive to receiving an entry to increase electrical stimulation therapy intensity that causes a present value of the second therapy parameter to be at or greater than a threshold value for the second therapy parameter, processing circuitry 214 may be configured to adjust the present value of the second therapy parameter from a first value of the second therapy parameter to a second value of the second therapy parameter. Processing circuitry 214 may also be configured to adjust a present value of the first therapy parameter from a first value of the first therapy parameter to a second value of the first therapy parameter. The first value of the first therapy parameter and the first value of the second therapy parameter set a first intensity and the second value of the first therapy parameter and the second value of the second therapy parameter set a second intensity, and the second intensity is greater than or equal to the first intensity. Processing circuitry 214 may cause delivery of therapy at the second intensity value.

As one example, the first therapy parameter is the pulse amplitude, and the second therapy parameter is the pulse width. As another example, the first therapy parameter is the pulse width, and the second therapy parameter is the pulse amplitude. Similarly, the first or second therapy parameters may be the pulse frequency, and the other parameters may be the pulse amplitude or pulse width. Moreover, in the above example, there is a first parameter and a second parameter. However, there may be more than two parameters. In such examples, processing circuitry 214 may keep substantially constant most of the parameters (e.g., all but one) and adjust a subset of the parameters (e.g., only one).

There may be various ways in which processing circuitry 214 may adjust the first and second therapy parameters. For example, to adjust the present value of the second therapy parameter from the first value of the second therapy parameter to the second value for the second therapy parameter, processing circuitry 214 may be configured to determine a scaling factor by which to decrease the first value of the second therapy parameter to the second value for the first therapy parameter. To adjust the present value of the first therapy parameter from the first value of the first therapy parameter to the second value of the first therapy parameter, processing circuitry 214 may be configured to increase the first value of the first therapy parameter to the second value of the first therapy parameter based on the determined scaling factor.

As one example, assume that the first therapy parameter is the pulse width and the second therapy parameter is the amplitude. In this example, processing circuitry 214 may keep the pulse width substantially constant while increasing the amplitude until the amplitude reaches its threshold value or an increase in the stimulation therapy intensity would cause the amplitude to be greater than its threshold value. In such examples, processing circuitry 214 may decrease the amplitude by a factor of 50% and increase the pulse width by a factor of 100%. In other words, processing circuitry 214 may half the amplitude and double the pulse width. In this example, the scaling factor is 2. For instance, to decrease the first value of the second therapy parameter to the second value of the second therapy parameter, processing circuitry 214 may multiply the first value of the second therapy parameter by an inverse of the scaling factor (e.g., multiply the first value of the second therapy parameter by one-half (½) to determine the second value of the second therapy parameter). Scaling factors other than 2 are possible.

Figure 3:
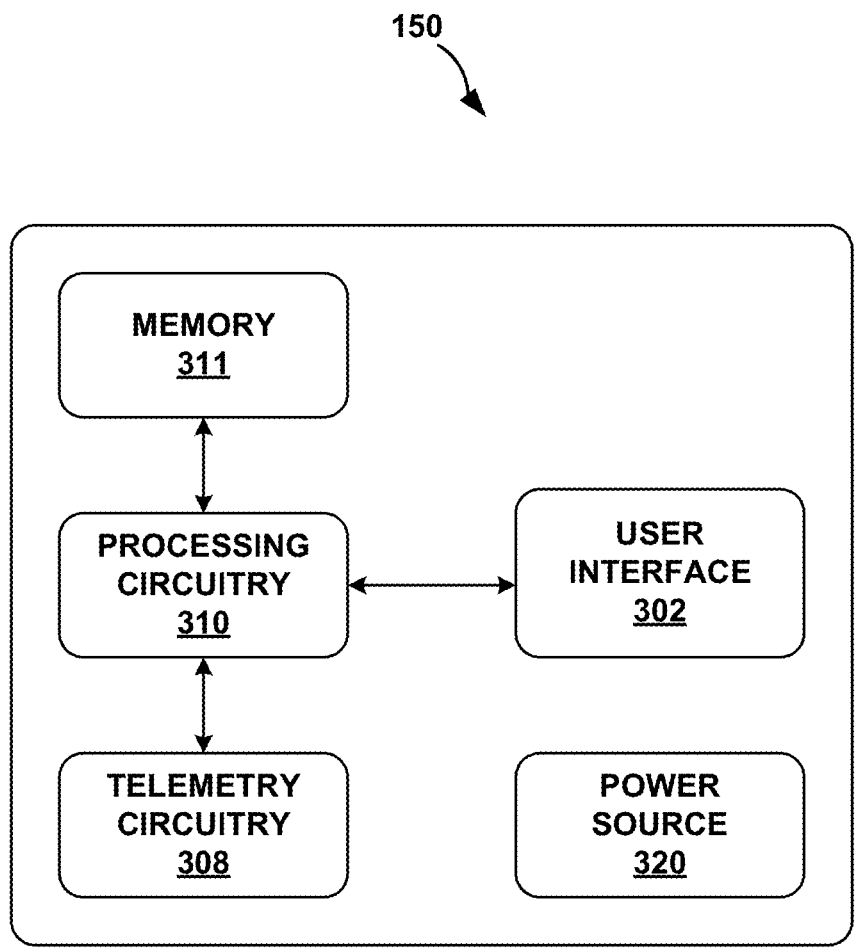
FIG. 3 is a block diagram of the external programmer of FIG. 1 for controlling delivery of therapy according to an example of the techniques of the disclosure.

FIG. 3 is a block diagram of the external programmer 150 of FIG. 1. Although programmer 150 may generally be described as a hand-held device, programmer 150 may be a larger portable device or a more stationary device. In addition, in other examples, programmer 150 may be included as part of an external charging device or include the functionality of an external charging device. As illustrated in FIG. 3, programmer 150 may include processing circuitry 310, memory 311, user interface 302, telemetry circuitry 308, and power source 320. Memory 311 may store instructions that, when executed by processing circuitry 310, cause processing circuitry 310 and external programmer 150 to provide the functionality ascribed to external programmer 150 throughout this disclosure. Each of these components, or modules, may include electrical circuitry that is configured to perform some or all of the functionality described herein. For example, processing circuitry 310 may include processing circuitry configured to perform the processes discussed with respect to processing circuitry 310.

In general, programmer 150 comprises any suitable arrangement of hardware, alone or in combination with software and/or firmware, to perform the techniques attributed to programmer 150, and processing circuitry 310, user interface 302, and telemetry circuitry 308 of programmer 150. In various examples, programmer 150 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 150 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processing circuitry 310 and telemetry circuitry 308 are described as separate modules, in some examples, processing circuitry 310 and telemetry circuitry 308 may be functionally integrated with one another. In some examples, processing circuitry 310 and telemetry circuitry 308 correspond to individual hardware units, such as ASICs, DSPs, FPGAs, or other hardware units.

Memory 311 (e.g., a storage device) may store instructions that, when executed by processing circuitry 310, cause processing circuitry 310 and programmer 150 to provide the functionality ascribed to programmer 150 throughout this disclosure. For example, memory 311 may include instructions that cause processing circuitry 310 to obtain a parameter set from memory or receive a user input and send a corresponding command to IMD 110, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry circuitry 308 may support wireless communication between IMD 110 and programmer 150 under the control of processing circuitry 310. Telemetry circuitry 308 may also be configured to communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 150 and IMD 110 include RF communication according to the 802.11 or Bluetooth specification sets or other standard or proprietary telemetry protocols. In this manner, other external devices may be capable of communicating with programmer 150 without needing to establish a secure wireless connection.

In some examples, processing circuitry 310 of external programmer 150 defines the parameters of electrical stimulation therapy, stored in memory 311, for delivering therapy to patient 105. In one example, processing circuitry 310 of external programmer 150, via telemetry circuitry 308, issues commands to IMD 110 causing IMD 110 to deliver electrical stimulation therapy via electrodes 232, 234 via leads 230.

In one or more examples, programmer 150 may be configured to perform one or more of the example techniques described in this disclosure. For instance, processing circuitry 310 may be configured to perform any of the example operations described above with respect to processing circuitry 214. In some examples, processing circuitry 310 may perform example operations or may be configured to perform the example operations together with circuitry of IMD 200 (e.g., processing circuitry 214). For ease, the following is described with respect to processing circuitry 310.

For example, responsive to each of a plurality of entries to increase electrical stimulation therapy intensity, processing circuitry 310 may be configured to hold a value of a first therapy parameter substantially constant and increase a value of a second therapy parameter. Responsive to receiving an entry to increase electrical stimulation therapy intensity that causes a present value of the second therapy parameter to be at or greater than a threshold value for the second therapy parameter, processing circuitry 310 may be configured to adjust the present value of the second therapy parameter from a first value of the second therapy parameter to a second value of the second therapy parameter. Processing circuitry 310 may also be configured to adjust a present value of the first therapy parameter from a first value of the first therapy parameter to a second value of the first therapy parameter. The first value of the first therapy parameter and the first value of the second therapy parameter set a first intensity and the second value of the first therapy parameter and the second value of the second therapy parameter set a second intensity, and the second intensity is greater than or equal to the first intensity. Processing circuitry 310 may cause delivery of therapy at the second intensity value. In some examples, processing circuitry 310 may output the intensity value to processing circuitry 214, and processing circuitry 214 may perform the example operations described above.

As one example, the first therapy parameter is the pulse amplitude, and the second therapy parameter is the pulse width. As another example, the first therapy parameter is the pulse width, and the second therapy parameter is the pulse amplitude. Similarly, the first or second therapy parameters may be the pulse frequency, and the other parameters may be the pulse amplitude or pulse width. Moreover, in the above example, there is a first parameter and a second parameter. However, there may be more than two parameters. In such examples, processing circuitry 310 may keep substantially constant most of the parameters (e.g., all but one) and adjust a subset of the parameters (e.g., only one).

There may be various ways in which processing circuitry 310 may adjust the first and second therapy parameters. For example, to adjust the present value of the second therapy parameter from the first value of the second therapy parameter to the second value for the second therapy parameter, processing circuitry 310 may be configured to determine a scaling factor by which to decrease the first value of the second therapy parameter to the second value for the first therapy parameter. To adjust the present value of the first therapy parameter from the first value of the first therapy parameter to the second value of the first therapy parameter, processing circuitry 310 may be configured to increase the first value of the first therapy parameter to the second value of the first therapy parameter based on the determined scaling factor.

As one example, assume that the first therapy parameter is the pulse width and the second therapy parameter is the amplitude. In this example, processing circuitry 310 may keep the pulse width substantially constant while increasing the amplitude until the amplitude reaches its threshold value or an increase in the stimulation therapy intensity would cause the amplitude to be greater than its threshold value. In such examples, processing circuitry 310 may decrease the amplitude by a factor of 50% and increase the pulse width by a factor of 100%. In other words, processing circuitry 310 may half the amplitude and double the pulse width. In this example, the scaling factor is 2. For instance, to decrease the first value of the second therapy parameter to the second value of the second therapy parameter, processing circuitry 310 may multiply the first value of the second therapy parameter by an inverse of the scaling factor (e.g., multiple the first value of the second therapy parameter by ½ to determine the second value of the second therapy parameter). Scaling factors other than 2 are possible.

Figure 4:
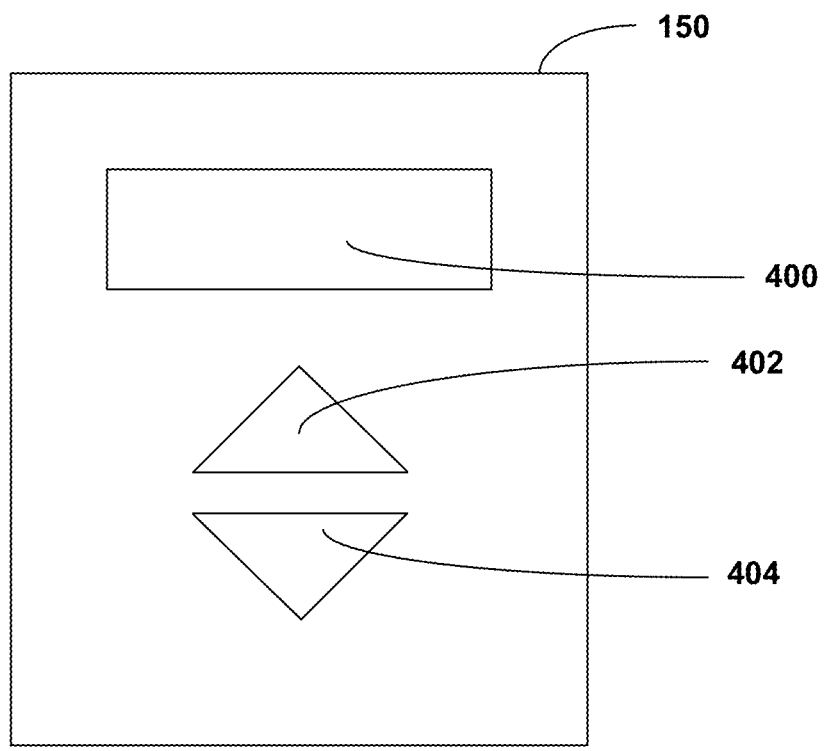
FIG. 4 is a conceptual diagram of the external programmer of FIG. 1.

FIG. 4 is a conceptual diagram of the external programmer of FIG. 1. For example, FIG. 4 illustrates an example of programmer 150 with which a user may interact. As described above, in one or more examples, the user may be able to adjust the electrical stimulation therapy intensity and not need to change each therapy parameter individually. Accordingly, as illustrated, programmer 150 may include an increase button 402 and a decrease button 404, and programmer 150 may include a display 400. Display 400 may display a value indicative of the current electrical stimulation therapy intensity. For example, the value may be the actual therapy intensity (e.g., in Joules or some unit of energy). In some examples, the value may be a unit-less value that represents the therapy intensity. For instance, display 400 may display a value between 0 to 10, where 0 represents the minimum therapy intensity that IMD 200 can deliver and 10 represents the maximum therapy intensity that IMD 200 can deliver. Other examples includes percentages, bar graphs, pie charts, and the like.

To increase the therapy intensity, the user may press down on increase button 402. To decrease the therapy intensity, the user may press down on decrease button 404. Although buttons are described as one example, the techniques are not limited. Dials or touch scales may be used instead of or in addition to buttons 402 and 404. Also, the dials and buttons 402 and 404 may be graphical dials and buttons or physical dials and buttons.

FIGS. 5A-5D are conceptual diagrams illustrating examples of stimulation waveforms. In the example techniques described in this disclosure, processing circuitry 214 and/or processing circuitry 310 is configured to determine therapy parameters based on the entry of the stimulation therapy intensity. One example way in which to determine the therapy parameters is to back calculate based on the desired stimulation therapy intensity. For example, the therapy parameters may be considered as forming a waveform of the delivered therapy. The area-under-the-curve of the stimulation waveform may define the stimulation therapy intensity. Processing circuitry 214 and/or processing circuitry 310 may determine which therapy parameters provide the stimulation therapy intensity based on the area-under-the-curve.

Figure 5A:
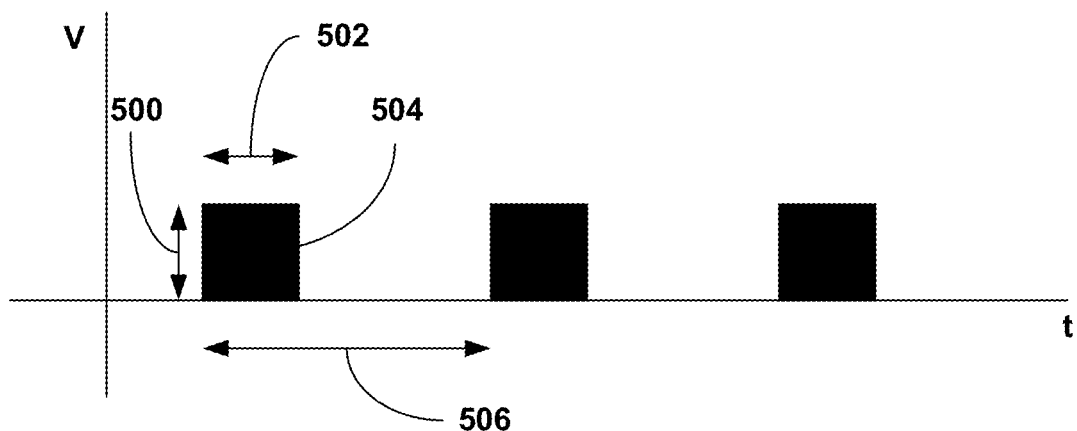
FIGS. 5A-5D are conceptual diagrams illustrating examples of stimulation waveforms.

For example, FIG. 5A illustrates a waveform of a plurality of rectangular pulses. In FIG. 5A, the waveform (e.g., pulse 504) is defined by pulse amplitude 500, pulse width 502, and time period 506 (e.g., the inverse of time period 506 is the frequency). The stimulation therapy intensity, for one pulse, is equal to amplitude 500 multiplied by pulse width 502, which indicates the area-under-the-curve of the waveform (e.g., pulse 504). When the result of the multiplication of amplitude 500 to pulse width 502 is divided by time period 506, the result is the average amount of stimulation therapy intensity within the time period. Also, when result of the division is multiplied by a certain amount of time, the result is total stimulation therapy intensity delivered within the certain amount of time.

Accordingly, based on above relationship of amplitude 500, pulse width 502, and time period 506 to the stimulation therapy intensity, it may be possible for processing circuitry 214 and/or 310 to determine the therapy parameters based on the input of the stimulation therapy intensity. Frequency also impacts the stimulation therapy intensity. For example, responsive to each of a plurality of entries to increase electrical stimulation therapy intensity, to hold a value of a first therapy parameter substantially constant (e.g., pulse width) and increase a value of a second therapy parameter (e.g., amplitude), processing circuitry 214 and/or 310 may be configured to determine a value of the increased electrical stimulation therapy intensity (e.g., determine what the increased electrical stimulation therapy intensity should be based on the user input).

Processing circuitry 214 and/or 310 may determine a scaling factor to apply to the second therapy parameter to increase the value of the second therapy parameter (e.g., determine by how much to increase the amplitude while keeping the pulse width substantially constant so that the stimulation therapy intensity is at the desired level). Processing circuitry 214 and/or 310 may determine that the increase in the second therapy parameter results in the second therapy parameter remaining less than the threshold value of the second therapy parameter (e.g., such that increasing the amplitude does not cause the amplitude to be greater than its threshold). In this case, processing circuitry 214 and/or 310 may increase the value of the second therapy parameter based on the determination that the increased value of the second therapy parameter is less than or equal to the threshold value for the second therapy parameter.

However, in some examples, processing circuitry 214 and/or 310 may determine that increasing the value of the second therapy parameter from its present value results in increasing the second therapy parameter to be greater than the threshold value of the second therapy parameter. As one example, processing circuitry 214 and/or 310 may determine an initial value for the second therapy parameter such that the initial value for the second therapy parameter and the value for the first therapy parameter result in an electrical simulation therapy intensity equal to the user input entry of the increased electrical stimulation therapy intensity, and determine that the initial value for the second therapy parameter is greater than the threshold value for the second therapy parameter.

As an example, assume that the threshold for the amplitude is 20 mA and the current amplitude is at 19.8 mA. In some examples, the user may enter a stimulation therapy intensity value, and processing circuitry 214 and/or 310 may determine an initial value that indicates what the amplitude should be so that the stimulation therapy intensity is equal to the entry of the increased stimulation therapy intensity. In some cases, processing circuitry 214 and/or 310 may determine the initial value is greater than the threshold value (e.g., the amplitude would be greater than 20 mA). In such cases, in accordance with one or more examples described in this disclosure, processing circuitry 214 and/or 310 may decrease the amplitude and increase the pulse width (as one example) so that stimulation therapy intensity is equal to the user input entry of the increased stimulation therapy intensity. In this way, the user experiences the actual desired stimulation therapy intensity without the amplitude going over the threshold. In some examples, rather than waiting until after the current is to become greater than the threshold upon an entry to increase the stimulation intensity, processing circuitry 214 and/or 310 may decrease the amplitude and increase the pulse width (again, as one example) when the amplitude reaches the threshold value.

Figure 5B:
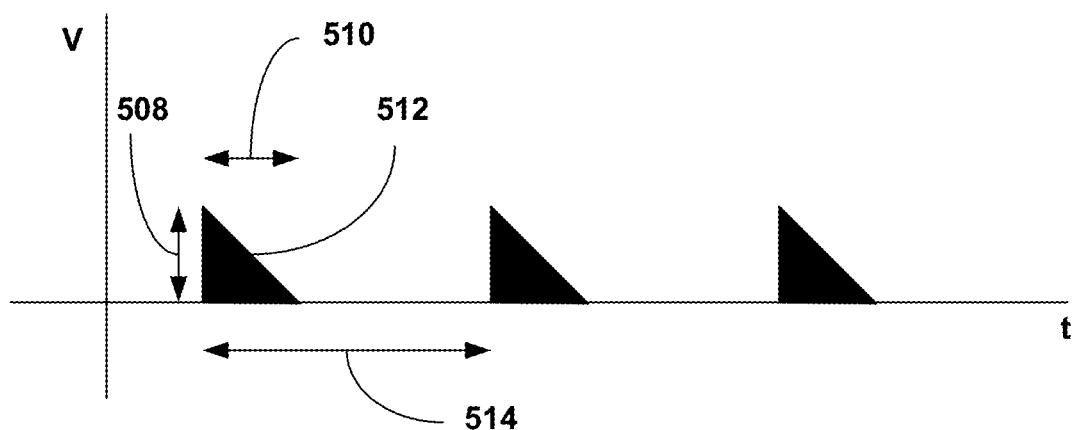
Figure 5C:
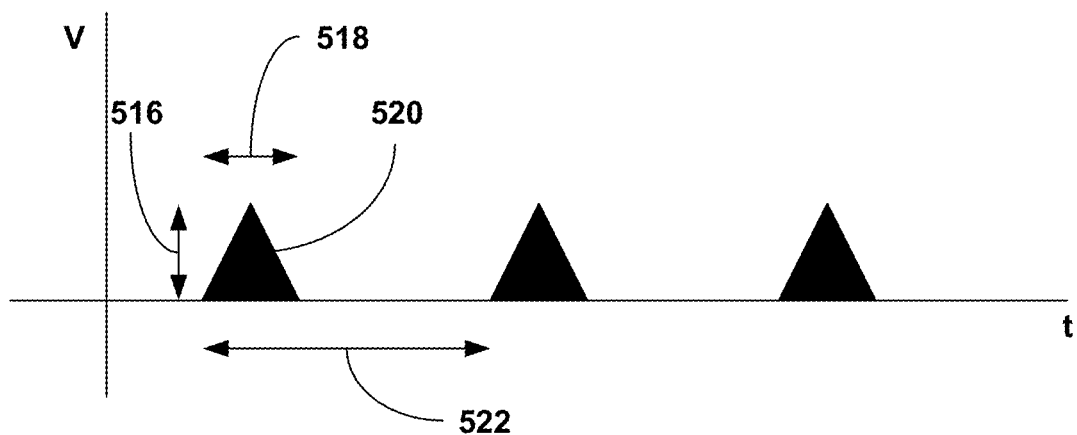
Figure 5D:
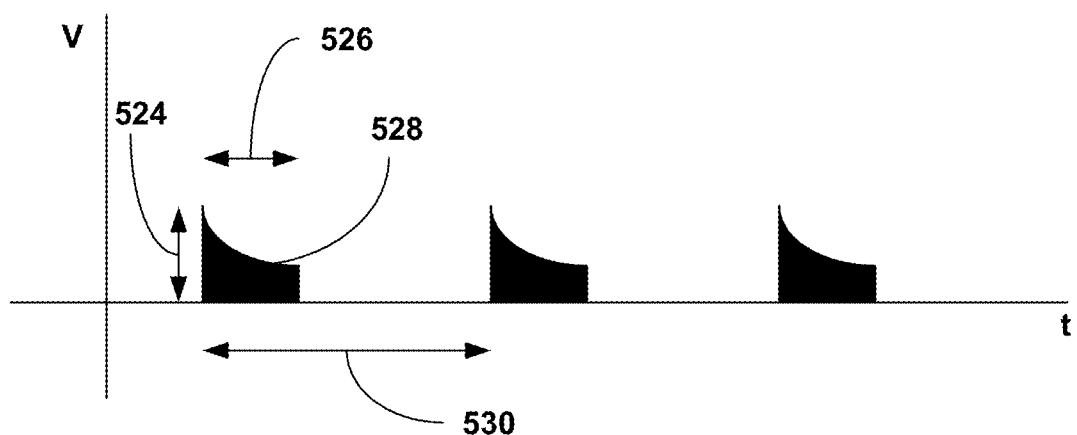

FIGS. 5B-5D illustrate different examples of waveforms. For instance, FIG. 5B illustrates amplitude 508, pulse width 510, and time period 514 for the waveform with triangle 512. For instance, FIG. 5C illustrates amplitude 516, pulse width 518, and time period 522 for the waveform with triangle 518. For instance, FIG. 5C illustrates amplitude 524, pulse width 526, and time period 530 for the waveform with decaying pulse 528. For each, the stimulation therapy intensity may be equal to the area-under-the-curve of each of the respective waveforms.

For example, as described above, responsive to receiving an entry to increase electrical stimulation therapy intensity that causes a present value of the second therapy parameter (e.g., amplitude) to be at or greater than a threshold value for the second therapy parameter, processing circuitry 214 and/or 310 may adjust the present value of the second therapy parameter from a first value of the second therapy parameter to a second value of the second therapy parameter (e.g., adjust the value of the amplitude downward from its present value), and adjust a present value of the first therapy parameter (e.g., pulse width) from a first value of the first therapy parameter to a second value of the first therapy parameter (e.g., adjust the value of the pulse width upward). In such examples, first value of the first therapy parameter and the first value of the second therapy parameter set a first intensity and the second value of the first therapy parameter and the second value of the second therapy parameter set a second intensity, and the second intensity is greater than or equal to the first intensity.

In one or more examples, the second intensity value is equal to an area-under-the-curve of a stimulation waveform defined by the second value for the first therapy parameter and the second value for the second therapy parameter. The first intensity value is equal to an area-under-the-curve of a stimulation waveform defined by the first value of the first therapy parameter and the first value for the second therapy parameter. For instance, the area-under-the-curve of the waveform prior to adjustment is equal to the first intensity value, and the area-under-curve of the waveform subsequent to adjustment is equal to the second intensity value. In this way, although processing circuitry 214 and/or 310 adjusts the present values of the first and second parameters from respective first values to respective second values, the result is that the stimulation therapy intensity is at the correct level.

Figure 6:
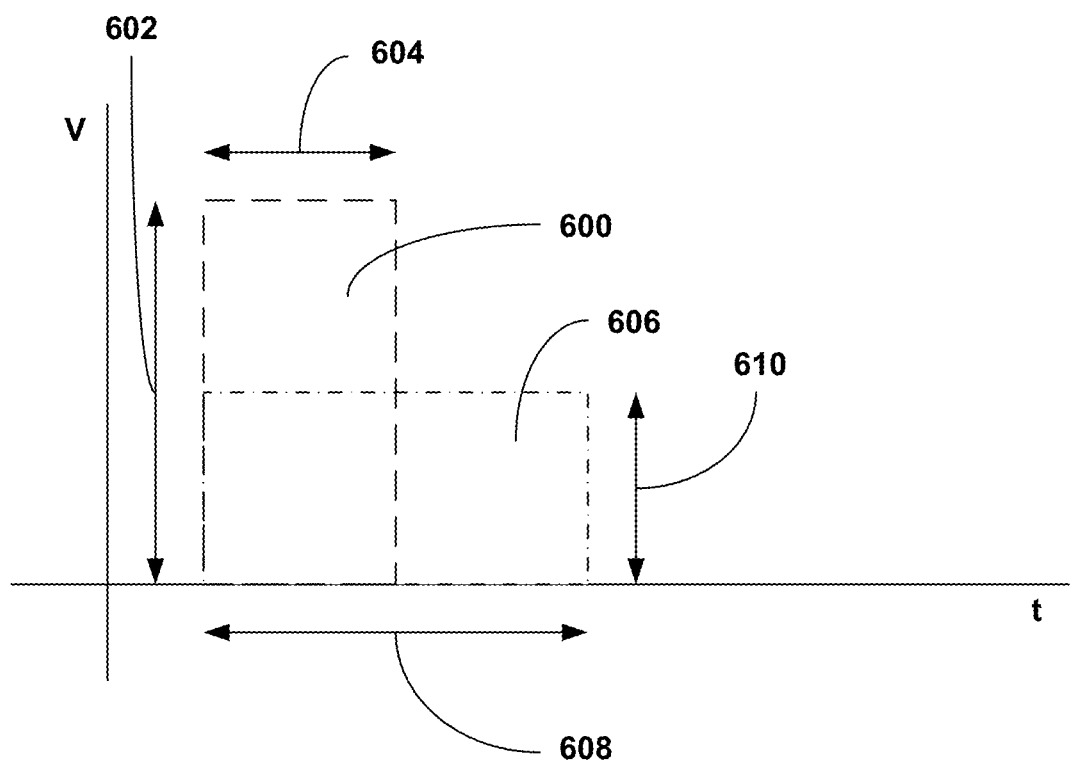
FIG. 6 is a conceptual diagram illustrating changes in amplitude and pulse width to keep electrical stimulation intensity substantially constant.

FIG. 6 is a conceptual diagram illustrating changes in amplitude and pulse width to keep electrical stimulation intensity substantially constant. For example, in a first instance, the present value of the amplitude parameter may be first amplitude value 602, and the present value of the pulse width parameter may be first pulse width value 608. Together, first amplitude value 602 and first pulse width value 608, define stimulation therapy intensity 600. If the present value of the amplitude parameter is adjusted from first amplitude value 602 to second amplitude value 610, and the present value of the pulse width parameter is adjusted from first pulse width value 604 to second pulse width value 608, then the stimulation therapy intensity changes from stimulation therapy intensity 600 to stimulation therapy intensity 606. In the example illustrated in FIG. 6, stimulation therapy intensity 600 is equal to stimulation therapy intensity 606.

Figure 7:
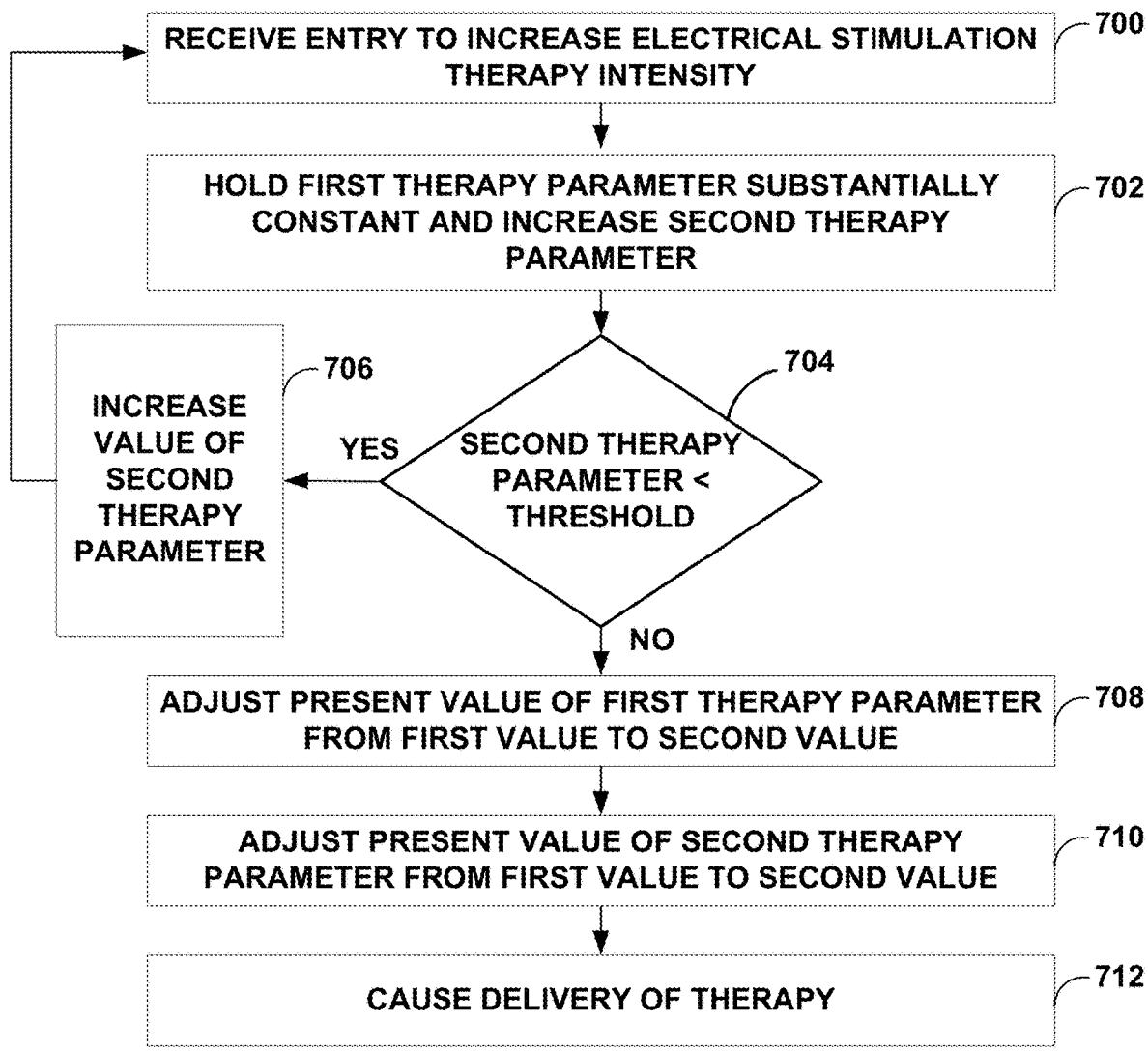
FIG. 7 is a flowchart illustrating an example operation in accordance with techniques of the disclosure.

FIG. 7 is a flowchart illustrating an example operation in accordance with techniques of the disclosure. For each of description, the example techniques are described with respect to processing circuitry performing the example techniques. Examples of the processing circuitry include processing circuitry 214, processing circuitry 310, and/or a combination of processing circuitry 214 and 310.

Processing circuitry may be configured to receive entry to increase electrical stimulation therapy intensity (e.g., based on user pushing increase button 402 of FIG. 4) (700). The processing circuitry may hold a value of a first therapy parameter substantially constant and increase a value of a second therapy parameter (702). The processing circuitry may determine whether increasing the value of the second therapy parameter would keep the second therapy parameter less than (or in some examples less than or equal to) a threshold value for the second therapy parameter (704). Based on a determination that the second therapy parameter is less than (or less than or equal to) to the threshold value for the second therapy parameter (YES of 704), the processing circuitry may increase the value of the second therapy parameter (706).

For example, the processing circuitry may determine a value of the increased electrical stimulation therapy intensity, and determine a scaling factor to apply to the value of the second therapy parameter to increase the value of the second therapy parameter (e.g., determine by how much to increase the value of the second therapy parameter to achieve the increased electrical stimulation therapy intensity assuming the first therapy parameter is substantially constant). In some examples, the scaling factor may be a substantially constant (e.g., increments of 0.2 mA for every entry to increase the stimulation therapy intensity). However, the scaling factor need not be a substantially constant value.

The processing circuitry may determine that the increased value of the second therapy parameter is less than or equal to the threshold value for the second therapy parameter, and increase the value of the second therapy parameter based on the determination that the increased value of the second therapy parameter is less than or equal to the threshold value for the second therapy parameter. The processing circuitry may repeat these operations as long as the second therapy parameter remains below or at the threshold value for the second therapy parameter. In this way, responsive to each of a plurality of entries to increase electrical stimulation therapy intensity, the processing circuitry may hold a value of a first therapy parameter substantially constant and increase a value of a second therapy parameter.

The processing circuitry may determine that increasing the value of the second therapy parameter from the present value results in increasing the value of the second therapy parameter to be greater than the threshold value of the second therapy parameter (NO of 704). For example, the processing circuitry may determine an initial value for the second therapy parameter such that the initial value for the second therapy parameter and the value for the first therapy parameter result in electrical simulation therapy intensity equal to the entry of the increased electrical stimulation therapy intensity, and determine that the initial value for the second therapy parameter is greater than the threshold value for the second therapy parameter.

In such cases, responsive to receiving an entry to increase electrical stimulation therapy intensity that causes a present value of the second therapy parameter to be at or greater than a threshold value for the second therapy parameter, the processing circuitry may adjust (e.g., decrease) the present value of the second therapy parameter from a first value of the second therapy parameter to a second value of the second therapy parameter (708), and adjust a present value of the first therapy parameter from a first value of the first therapy parameter to a second value of the first therapy parameter (710). The first value of the first therapy parameter and the first value of the second therapy parameter set a first intensity and the second value of the first therapy parameter and the second value of the second therapy parameter set a second intensity. Also, the second intensity is greater than or equal to the first intensity. For example, the second intensity value is equal to an area-under-the-curve of a stimulation waveform defined by the second value for the first therapy parameter and the second value for the second therapy parameter, and the first intensity value is equal to an area-under-the-curve of a stimulation waveform defined by the first value of the first therapy parameter and the first value for the second therapy parameter.

As one example, to adjust the present value of the second therapy parameter from the first value of the second therapy parameter to the second value for the second therapy parameter, the processing circuitry may determine a scaling factor by which to decrease the first value of the second therapy parameter to the second value for the first therapy parameter (e.g., reduce the value of the second therapy parameter by half). To adjust the present value of the first therapy parameter from the first value of the first therapy parameter to the second value of the first therapy parameter, the processing circuitry may increase the first value of the first therapy parameter to the second value of the first therapy parameter based on the determined scaling factor (e.g., increase the value of the first therapy parameter by a factor of two). In this example, the scaling factor is two. For instance, to decrease the first value of the second therapy parameter to the second value of the second therapy parameter based on the determined scaling factor, the processing circuitry may multiply the first value of the second therapy parameter by an inverse of the scaling factor (e.g., to obtain half the value of the second therapy parameter, the processing circuitry may multiply the present value of the second therapy parameter by 0.5, which is the inverse of the scaling factor of 2). Other scaling factors can be used.

The processing circuitry may cause delivery of therapy at the second intensity value (712). As one example, processing circuitry 310 may output instructions to processing circuitry 214 that include the second value of the first therapy parameter and the second value of the second therapy parameter and instruct processing circuitry 214 to cause stimulation generator 211 to output therapy based on the second value of the first therapy parameter and the second value of the second therapy parameter. As another example, processing circuitry 214 may have determined the second values for the first and second therapy parameters and may cause stimulation generator 211 to output therapy based on the second value of the first therapy parameter and the second value of the second therapy parameter.

Figure 8:
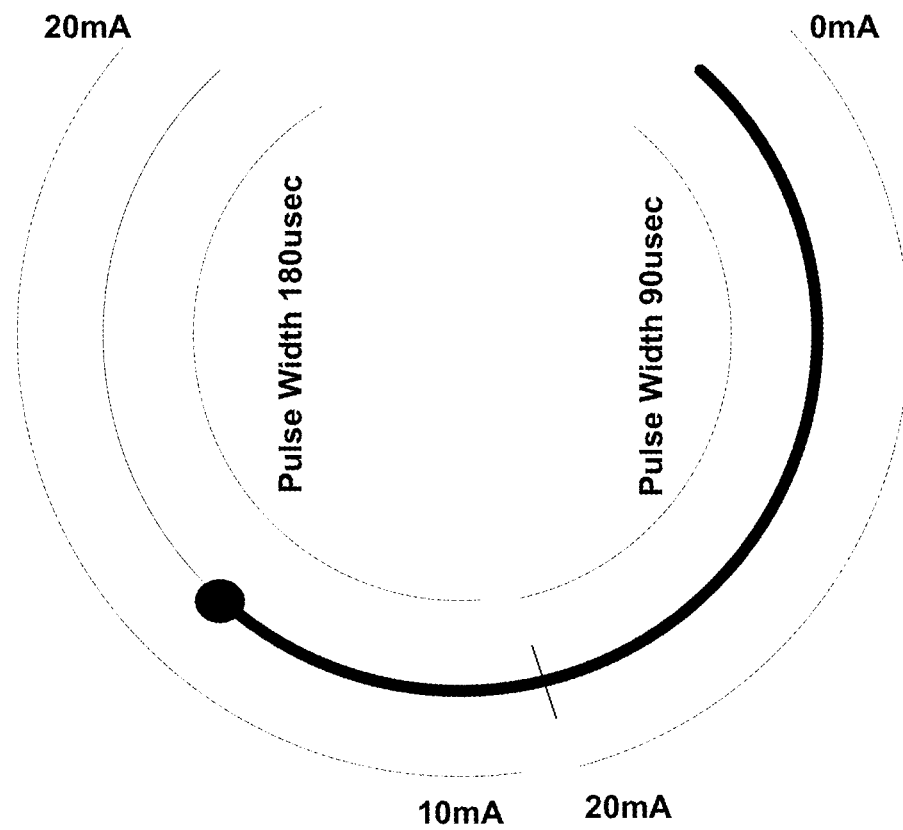
FIG. 8 is a conceptual diagram illustrating an example of adjusting parameters in accordance with techniques of the disclosure.

FIG. 8 is a conceptual diagram illustrating an example of adjusting parameters in accordance with techniques of the disclosure. For example, the right side of FIG. 8 illustrates that while the amplitude is less than 20 mA, the pulse width is kept substantially constant at 90 micro-seconds. As the amplitude is increased, and increases past 20 mA, the range of the amplitude is from 10 mA to 20 mA, and the pulse width is increased to 180 micro-seconds.

FIGS. 9-14 are images illustrating example positions of electrodes that can be used to control therapy. For example, FIGS. 9-14 illustrate example uses cases that may utilize the techniques described in this disclosure. A clinician and patient 105 may utilize the techniques described with respect to FIGS. 9-14 to determine the proper therapy parameters. For example, FIGS. 9-14 illustrate a workflow that the client and patient 105 may implement in accordance with techniques described in this disclosure. The workflow is described with respect to programmer 150, but the example techniques are not so limited. Rather than programmer 150 determining the therapy parameters, programmer 150 may output information to IMD 200 indicating a change in stimulation therapy intensity, and IMD 200 may be configured to determine the therapy parameters.

FIGS. 9-14 illustrate two leads 900A and 900B implanted within patient 105 and proximate to spinal cord 120 of patient 105. Leads 900A and 900B include eight electrodes each. The electrodes may be configured to be anodes or cathodes. Lead 900A may be considered as the midline lead. Also, for reference, the T9 plate (i.e., T9 vertebrae) of patient 105 is illustrated. Above the T9 plate is the T10 plate, and below the T9 plate is the T8 plate.

Figure 9:
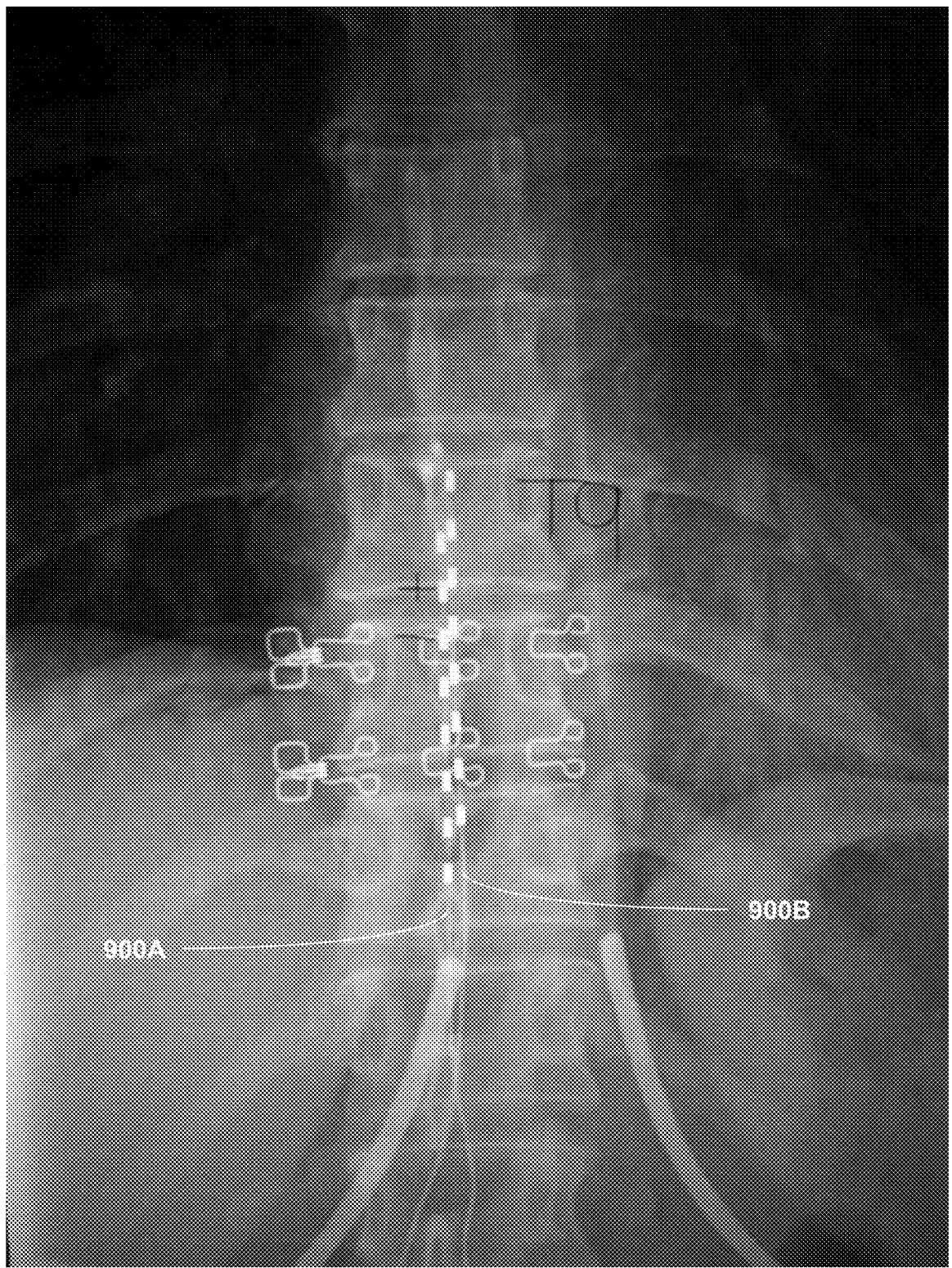
FIGS. 9-14 are images illustrating example positions of electrodes that can be used to control therapy.

The workflow may begin in state 1, which is described with respect to FIG. 9. In state 1, patient 105 may be in the supine position, and the clinician may identify the midline lead (e.g., lead 900A). The clinician may configure the electrode of lead 900A that is at the T10 superior endplate as the cathode. For instance, FIG. 9 illustrates the – sign next to the electrode that is at the T10 superior endplate, identifying that electrode as the cathode. This seems to be a very effective programming location for cathode placement. The clinician may configure the electrode of lead 900A that is directly superior to the cathode as the anode. For instance, FIG. 9 illustrates the – sign next to the electrode that is the anode, which is directly superior to the electrode with the + sign (e.g., cathode).

Programmer 150 may be initially set with a pulse width of 90 micro-seconds and a frequency of 1 kHz. The user (e.g., clinician or patient 105) may increase stimulation therapy intensity (e.g., by pressing button 402 of FIG. 4). In one or more examples, in response to the user increasing stimulation therapy intensity, programmer 150 may hold the pulse width and frequency substantially constant and increase the amplitude. The user may keep pressing button 402, and programmer 150 may keep increasing amplitude while holding pulse width and frequency substantially constant. The user may repeat this process until patient 105 experiences a perception threshold (e.g., Valsalva or coughing).

However, if increasing the amplitude would result in an out of range amplitude (e.g., amplitude becomes greater than threshold), programmer 150 may automatically increase the pulse width and in accordance with the example techniques and decrease the amplitude to achieve the desired stimulation therapy intensity. In some examples, programmer 150 may increase the pulse width to the lowest level that allows paresthesia without having the amplitude become greater than the threshold value. The user may then keep increasing the stimulation therapy intensity until paresthesia or amplitude is greater than threshold value. In response, programmer 150 may increase the pulse width and decrease the amplitude, and this process keeps repeating until patient 105 experiences paresthesia or both the pulse width and amplitude have reached respective threshold values without patient 105 experiencing paresthesia. The example pulse width values that programmer 150 may set the pulse width to are 90 micro-seconds, 120 micro-seconds, 150 microseconds, 180 micro-seconds, 200 micro-seconds, and 220 micro-seconds. In general, a decrease in pulse width (compared to 220 micro-seconds) may result in decreased battery depletion of power source 219.

Figure 10:
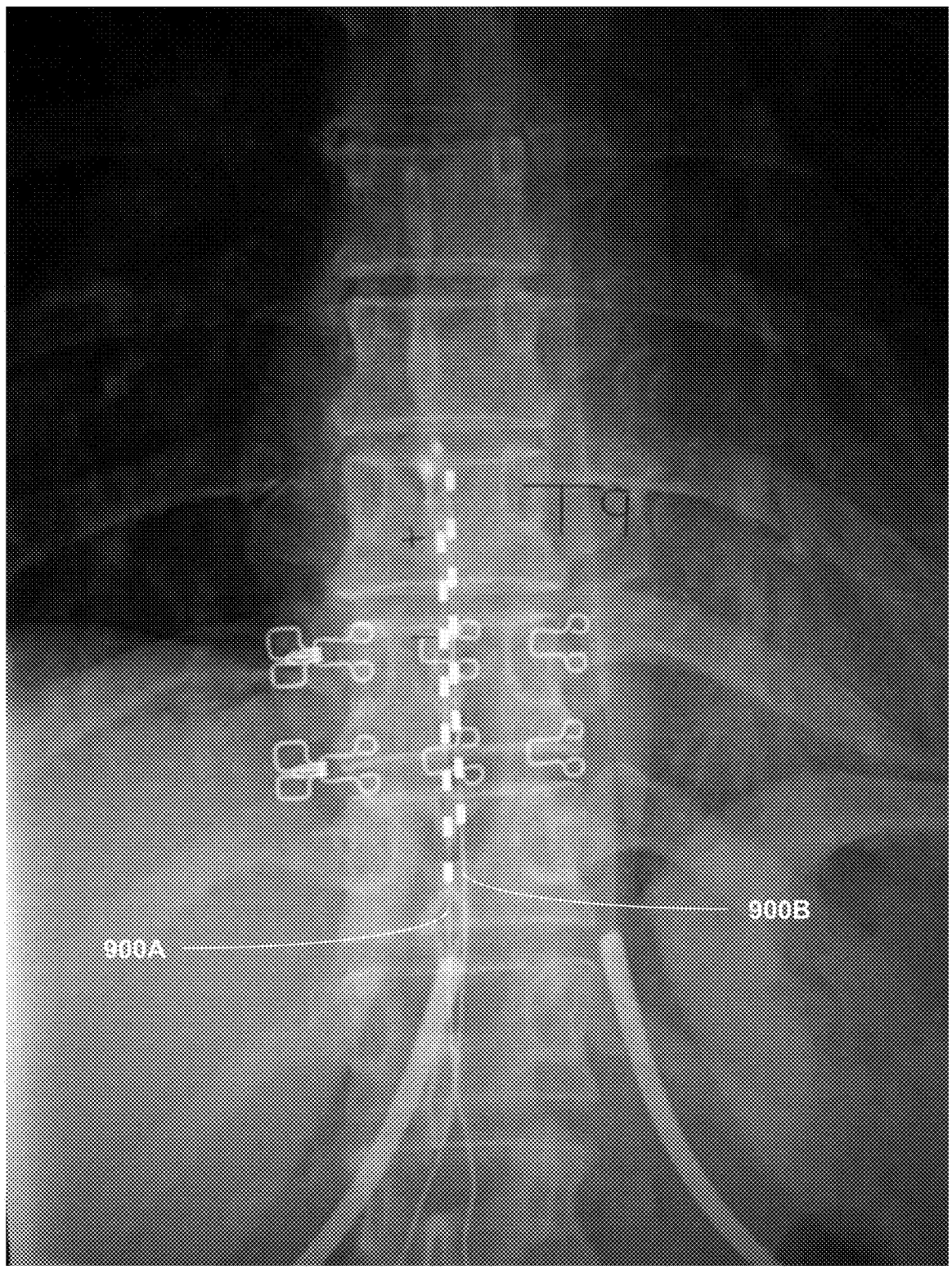

If patient 105 does not experience paresthesia with state 1 (e.g., pulse width and amplitude are at threshold values), the clinician may transition patient 105 to state 2, described with respect to FIG. 10. Similar to state 1, in state 2, patient 105 is in the supine position and lead 900A is the midline lead. The cathode is the electrode at the T10 superior endplate. However, unlike state 1, the anode is the electrode that is two electrodes superior to the cathode. For instance, as illustrated in FIG. 10, the cathode is still at the superior end plate of T10 but the anode is 2 electrodes above. In FIG. 10, the cathode has not moved from the example in FIG. 9, and only the anode has moved superiorly 1 electrode space.

The clinician and patient 105 may then perform the same operations as described with respect to FIG. 9 until patient 105 experiences paresthesia or both pulse width and amplitude are at their respective threshold values. Similar to state 1, a decrease in pulse width may assist in decreased battery depletion of power source 219. In some examples, the spreading out of the polarities may assist in decrease of battery depletion of power source 219.

Figure 11:
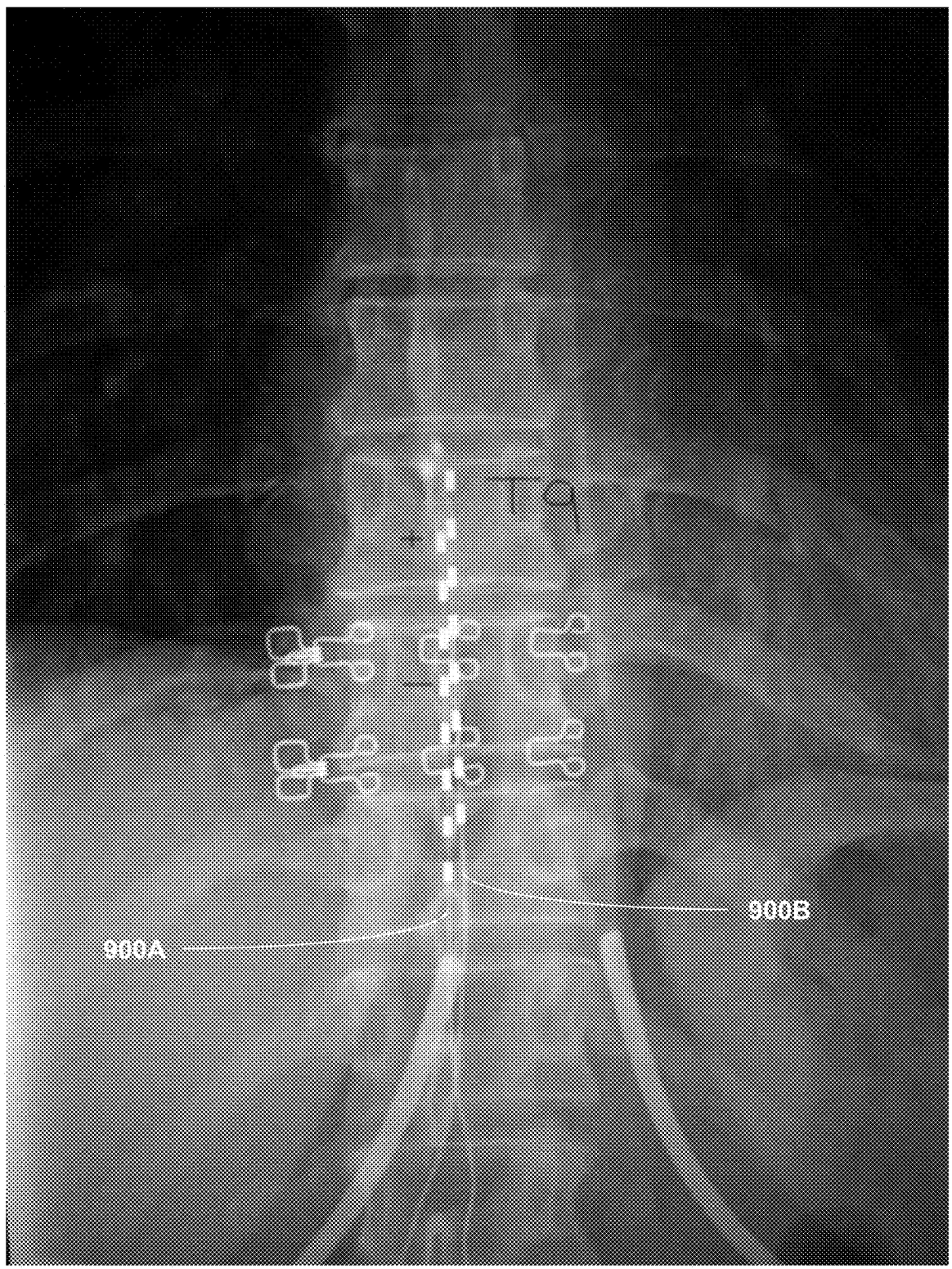

If patient 105 does not experience paresthesia with state 2 (e.g., pulse width and amplitude are at threshold values), the clinician may transition patient 105 to state 3, described with respect to FIG. 11. Similar to states 1 and 2, in state 3, patient 105 is in the supine position and lead 900A is the midline lead.

However, unlike states 1 and 2, the cathode is the electrode inferior to the T10 superior endplate. For example, the cathode should be the electrode at the upper to mid body to T10 plate, as shown by the – sign in FIG. 11. Also, the anode is the electrode that is three electrodes superior to the cathode. For instance, as illustrated in FIG. 11, the electrode with the – sign next to it is three electrodes down from the electrode with the + sign next to it. This should place the anode at the upper to mid body to T9 plate, as shown by the + sign in FIG. 11.

The clinician and patient 105 may then perform the same operations as described with respect to FIGS. 9 and 10 until patient 105 experiences paresthesia or both pulse width and amplitude are at their respective threshold values. Similar to states 1 and 2, a decrease in pulse width may assist in decreased battery depletion of power source 219. In some examples, the spreading out of the polarities may assist in decrease the rate of battery depletion of power source 219.

Figure 12:
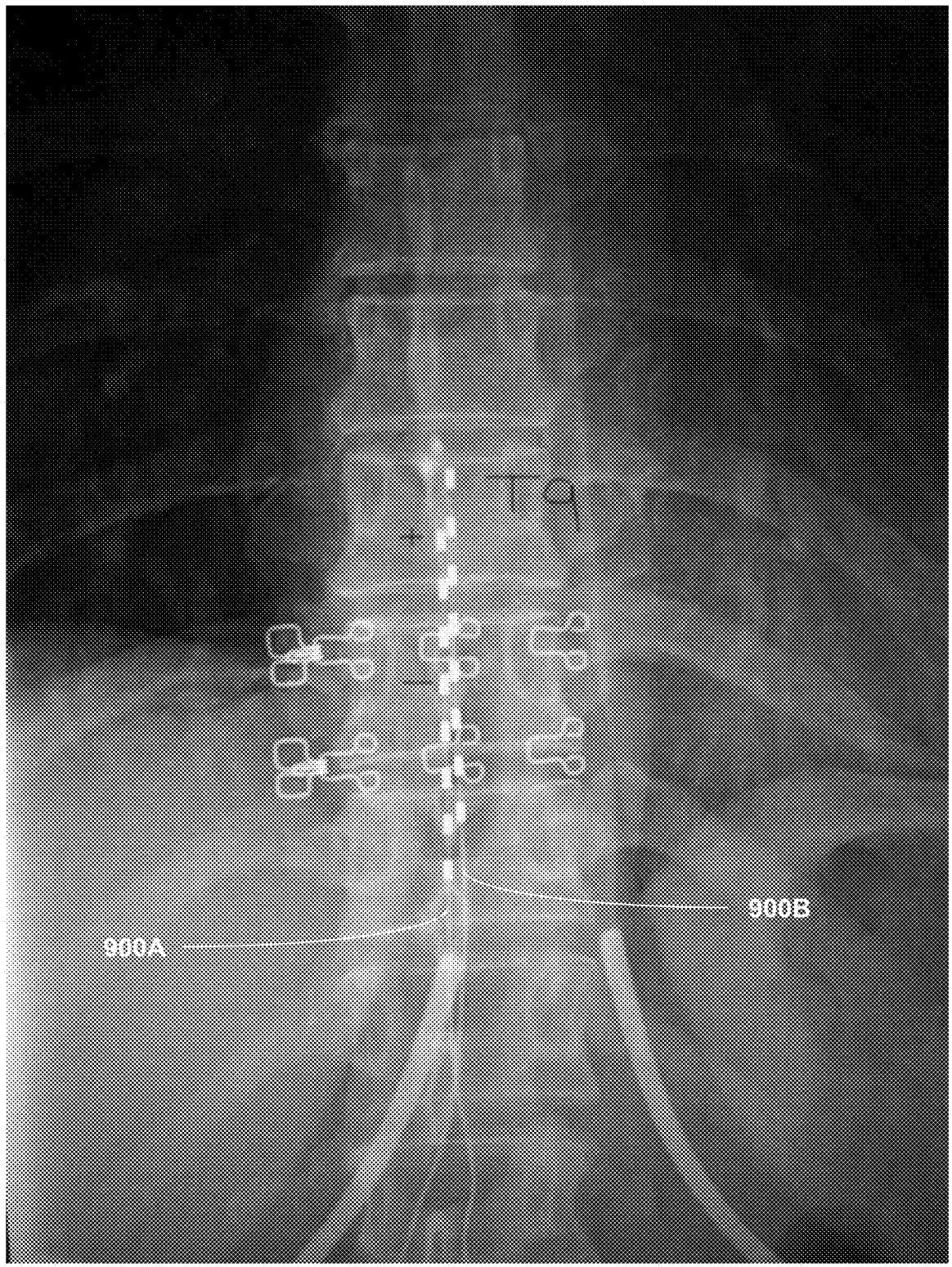

If patient 105 does not experience paresthesia with state 3 (e.g., pulse width and amplitude are at threshold values), the clinician may transition patient 105 to state 4, described with respect to FIG. 12. Similar to states 1-3, in state 4, patient 105 is in the supine position. However, in this example, the clinician may try and identify the most midline lead if possible.

The cathode and anode placement of the electrodes for state 4 is the same as state 3. If it is assumed that the midline lead is still lead 900A, then FIG. 12 and FIG. 11 are the same.

However, unlike states 1-3, in state 4, the user may initialize the therapy parameters to 300 micro-seconds pulse width and 800 Hz frequency. Similar to above, responsive to entry to increase stimulation therapy intensity, programmer 150 may increase the amplitude but hold the pulse width substantially constant at 300 micro-seconds and frequency substantially constant at 800 Hz. If the amplitude reaches its threshold without patient 105 experiencing a perception threshold (e.g., Valsalva), rather than adjusting pulse width or frequency, the clinician may transition patient 105 to state 5.

Figure 13:
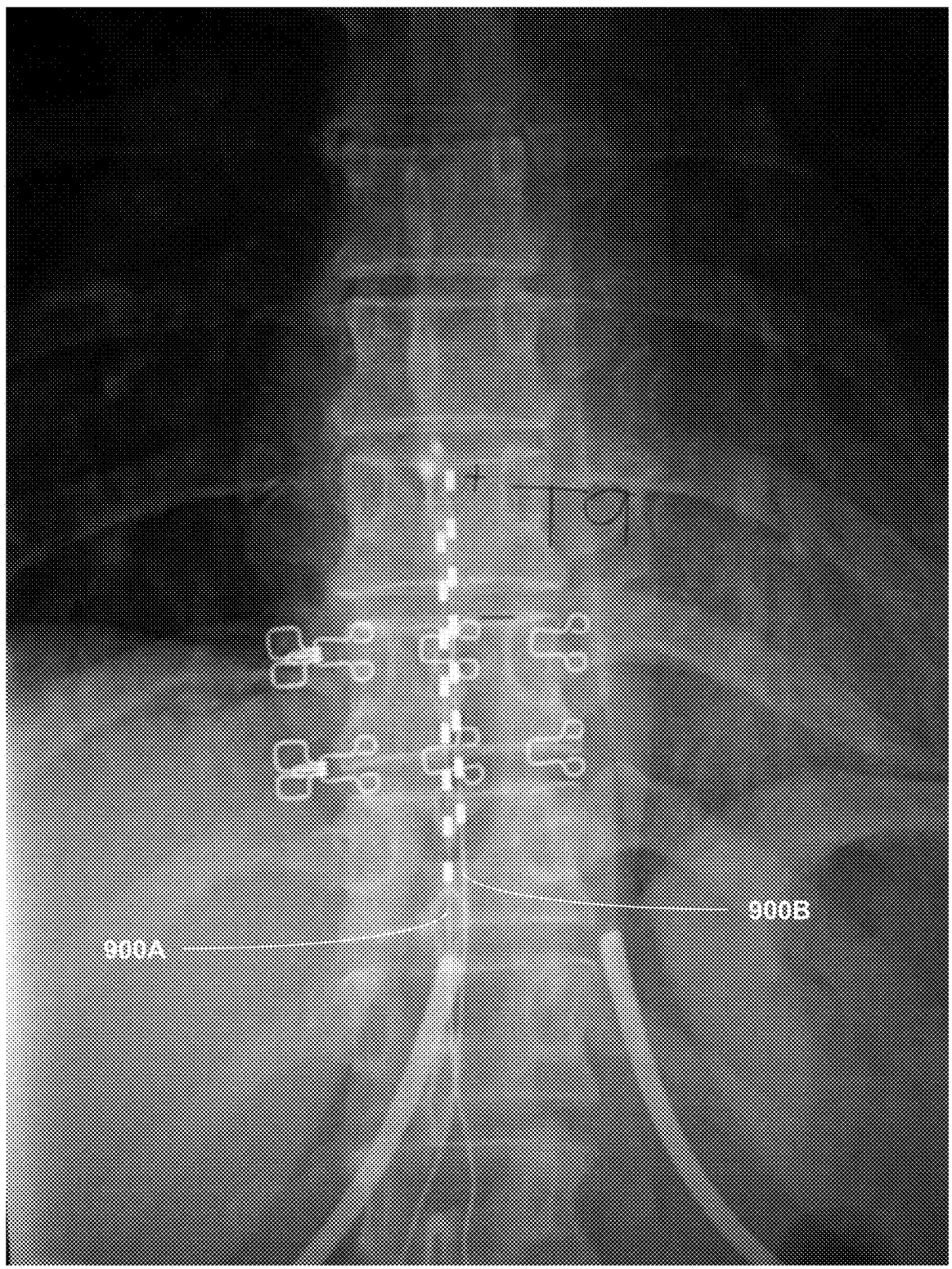

State 5 is described with respect to FIG. 13. State 5 is similar to state 3. However, the cathode and anode electrodes are on lead 900B, instead of lead 900A. The clinician and patient 105 may perform the same operations described above with respect to state 3, as part of the operations for state 5.

Figure 14:
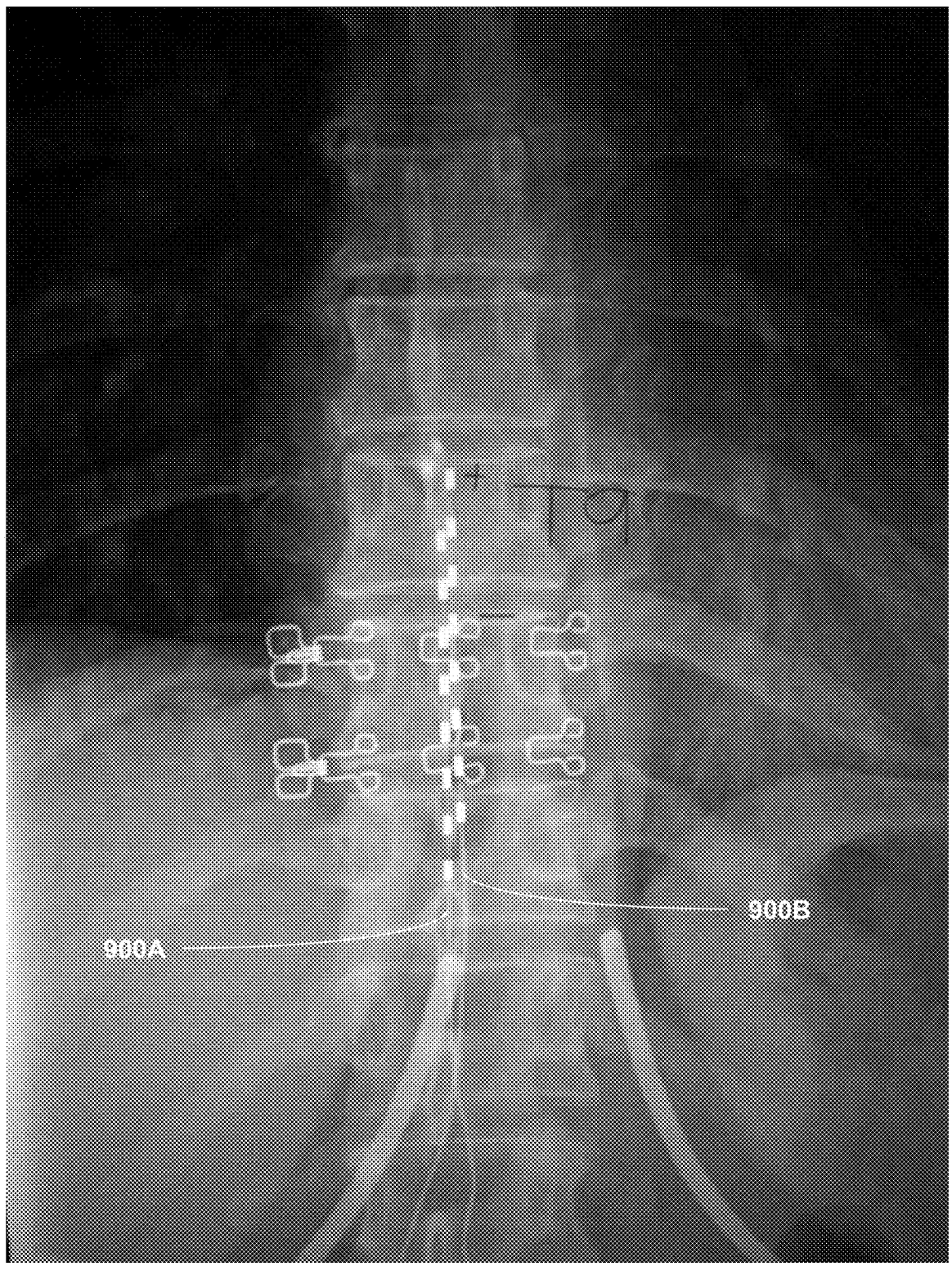

If patient 105 does not experience paresthesia with state 5 (e.g., pulse width and amplitude are at threshold values), the clinician may transition patient 105 to state 6, described with respect to FIG. 14. In state 6, patient 105 is in the supine position. However, in this example, the clinician may try and identify the most midline lead if possible.

The cathode and anode placement of the electrodes for state 6 is the same as state 5. If it is assumed that the midline lead is still lead 900B, then FIG. 14 and FIG. 13 are the same.

In state 6, the user may initialize the therapy parameters to 300 micro-seconds pulse width and 800 Hz frequency. Similar to above (e.g., state 4), responsive to user input entry to increase stimulation therapy intensity, programmer 150 may increase the amplitude but hold the pulse width substantially constant at 300 micro-seconds and frequency substantially constant at 800 Hz until patient 105 experiences perception threshold (e.g., Valsalva).

The following examples are example systems, devices, and methods described herein. Example 1: A method comprising: responsive to each of a plurality of user input entries to increase electrical stimulation therapy intensity, holding a value of a first therapy parameter substantially constant and increasing a value of a second therapy parameter; responsive to receiving a user input entry to increase electrical stimulation therapy intensity that causes a present value of the second therapy parameter to be at or greater than a threshold value for the second therapy parameter, adjusting the present value of the second therapy parameter from a first value of the second therapy parameter to a second value of the second therapy parameter, and adjusting a present value of the first therapy parameter from a first value of the first therapy parameter to a second value of the first therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity; and causing delivery of therapy at the second intensity.

Example 2: the method of example 1, wherein the first therapy parameter comprises a pulse amplitude and the second therapy parameter comprises a pulse width.

Example 3: the method of example 1, wherein the first therapy parameter comprises a pulse width and the second therapy parameter comprises a pulse amplitude.

Example 4: the method of any of examples 1-3, wherein adjusting the present value of the second therapy parameter from the first value of the second therapy parameter to the second value for the second therapy parameter comprises determining a scaling factor by which to decrease the first value of the second therapy parameter to the second value for the first therapy parameter, and wherein adjusting the present value of the first therapy parameter from the first value of the first therapy parameter to the second value of the first therapy parameter comprises increasing the first value of the first therapy parameter to the second value of the first therapy parameter based on the determined scaling factor.

Example 5: the method of example 4, wherein decreasing the first value of the second therapy parameter to the second value of the second therapy parameter based on the determined scaling factor comprises multiplying the first value of the second therapy parameter by an inverse of the scaling factor.

Example 6: The method of any of examples 1-5, wherein the second intensity is equal to an area-under-the-curve of a stimulation waveform defined by the second value for the first therapy parameter and the second value for the second therapy parameter, and wherein the first intensity is equal to an area-under-the-curve of a stimulation waveform defined by the first value of the first therapy parameter and the first value for the second therapy parameter.

Example 7: the method of any of examples 1-6, wherein responsive to each of a plurality of user input entries to increase electrical stimulation therapy intensity, holding a value of a first therapy parameter substantially constant and increasing a value of a second therapy parameter comprises determining a value of the increased electrical stimulation therapy intensity, determining a scaling factor to apply to the value of the second therapy parameter to increase the value of the second therapy parameter based on the value of the increased electrical stimulation therapy intensity, determining that the increased value of the second therapy parameter is less than or equal to the threshold value for the second therapy parameter, and increasing the value of the second therapy parameter based on the determination that the increased value of the second therapy parameter is less than or equal to the threshold value for the second therapy parameter.

Example 8: the method of any of examples 1-7, further comprising determining that increasing the value of the second therapy parameter from the present value results in increasing the value of the second therapy parameter to be greater than the threshold value for the second therapy parameter.

Example 9: the method of example 8, wherein determining that increasing the value of the second therapy parameter from the present value results in increasing the value of the second therapy parameter to be greater than the threshold value for the second therapy parameter comprises determining an initial value for the second therapy parameter such that the initial value for the second therapy parameter and the value for the first therapy parameter result in electrical simulation therapy intensity equal to the value of the increased electrical stimulation therapy intensity, and determining that the initial value for the second therapy parameter is greater than the threshold value for the second therapy parameter to determine that increasing the value of the second therapy parameter from the present value results in increasing the value of the second therapy parameter to be greater than the threshold value for the second therapy parameter.

Example 10: the method of example 1, further comprising selecting a first cathode electrode and a first anode electrode, wherein causing delivery of therapy at the second intensity comprises causing delivery of therapy at the second intensity utilizing the first cathode electrode and the first anode electrode, the method further comprising based on a determination that the present value of the first therapy parameter and the second therapy parameter are at respective thresholds, selecting a second cathode electrode and a second anode electrode; responsive to each of a plurality of user input entries to increase electrical stimulation therapy intensity subsequent to the selection of the second cathode and the second anode electrode, holding the value of a first therapy parameter substantially constant and increasing a value of a second therapy parameter; causing delivery of therapy based on the first therapy parameter and the increased value of the second therapy parameter.

Example 11: a system comprising: a memory configured to store one or more threshold values for one or more therapy parameters; and processing circuitry configured to: responsive to each of a plurality of user input entries to increase electrical stimulation therapy intensity, hold a value of a first therapy parameter substantially constant and increase a value of a second therapy parameter; responsive to receiving a user input entry to increase electrical stimulation therapy intensity that causes a present value of the second therapy parameter to be at or greater than a threshold value stored in memory for the second therapy parameter, adjust the present value of the second therapy parameter from a first value of the second therapy parameter to a second value of the second therapy parameter, and adjust a present value of the first therapy parameter from a first value of the first therapy parameter to a second value of the first therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity; and cause delivery of therapy at the second intensity.

Example 12: the system of example 11, wherein the first therapy parameter comprises a pulse amplitude and the second therapy parameter comprises a pulse width. Example 13: the system of example 11, wherein the first therapy parameter comprises a pulse width and the second therapy parameter comprises a pulse amplitude.

Example 14: the system of any of examples 11-13, wherein to adjust the present value of the second therapy parameter from the first value of the second therapy parameter to the second value for the second therapy parameter, the processing circuitry is configured to determine a scaling factor by which to decrease the first value of the second therapy parameter to the second value for the first therapy parameter, and wherein to adjust the present value of the first therapy parameter from the first value of the first therapy parameter to the second value of the first therapy parameter, the processing circuitry is configured to increase the first value of the first therapy parameter to the second value of the first therapy parameter based on the determined scaling factor.

Example 15: the system of example 14, wherein to decrease the first value of the second therapy parameter to the second value of the second therapy parameter based on the determined scaling factor, the processing circuitry is configured to multiply the first value of the second therapy parameter by an inverse of the scaling factor.

Example 16: the system of any of examples 11-15, wherein the second intensity is equal to an area-under-the-curve of a stimulation waveform defined by the second value for the first therapy parameter and the second value for the second therapy parameter, and wherein the first intensity is equal to an area-under-the-curve of a stimulation waveform defined by the first value of the first therapy parameter and the first value for the second therapy parameter.

Example 17: the system of any of examples 11-16, wherein to hold a value of a first therapy parameter substantially constant and increase a value of a second therapy parameter responsive to each of a plurality of user input entries to increase electrical stimulation therapy intensity, the processing circuitry is configured to: determine a value of the increased electrical stimulation therapy intensity; determine a scaling factor to apply to the value of the second therapy parameter to increase the value of the second therapy parameter based on the value of the increased electrical stimulation therapy intensity; determine that the increased value of the second therapy parameter is less than or equal to the threshold value for the second therapy parameter; and increase the value of the second therapy parameter based on the determination that the increased value of the second therapy parameter is less than or equal to the threshold value for the second therapy parameter.

Example 18: the system of any of examples 11-17, wherein the processing circuitry is configured to: determine that increasing the value of the second therapy parameter from the present value results in increasing the value of the second therapy parameter to be greater than the threshold value for the second therapy parameter.

Example 19: the system of example 18, wherein to determine that increasing the value of the second therapy parameter from the present value results in increasing the value of the second therapy parameter to be greater than the threshold value for the second therapy parameter, the processing circuitry is configured to: determine an initial value for the second therapy parameter such that the initial value for the second therapy parameter and the value for the first therapy parameter result in electrical simulation therapy intensity equal to the value of the increased electrical stimulation therapy intensity; and determine that the initial value for the second therapy parameter is greater than the threshold value for the second therapy parameter to determine that increasing the value of the second therapy parameter from the present value results in increasing the value of the second therapy parameter to be greater than the threshold value for the second therapy parameter Example 20: the system of any of examples 11-19, wherein the processing circuitry is configured to select a first cathode electrode and a first anode electrode, wherein to cause delivery of therapy at the second intensity, the processing circuitry is configured to cause delivery of therapy at the second intensity utilizing the first cathode electrode and the first anode electrode, and wherein the processing circuitry is further configured to: based on a determination that the present value of the first therapy parameter and the second therapy parameter are at respective thresholds, select a second cathode electrode and a second anode electrode; responsive to each of a plurality of user input entries to increase electrical stimulation therapy intensity subsequent to the selection of the second cathode and the second anode electrode, hold the value of a first therapy parameter substantially constant and increasing a value of a second therapy parameter; and cause delivery of therapy based on the first therapy parameter and the increased value of the second therapy parameter.

Example 21: The system of any of examples 11-20, further comprising an implantable medical device (IMD), wherein the IMD comprises the memory and the processing circuitry.

Example 22: a computer-readable storage medium comprising instructions to cause a programmable processor to: responsive to each of a plurality of user input entries to increase electrical stimulation therapy intensity, hold a value of a first therapy parameter substantially constant and increasing a value of a second therapy parameter; responsive to receiving a user input entry to increase electrical stimulation therapy intensity that causes a present value of the second therapy parameter to be at or greater than a threshold value for the second therapy parameter, adjust the present value of the second therapy parameter from a first value of the second therapy parameter to a second value of the second therapy parameter, and adjust a present value of the first therapy parameter from a first value of the first therapy parameter to a second value of the first therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity; and cause delivery of therapy at the second intensity.

Example 23: the computer-readable storage medium of example 22, wherein the first therapy parameter comprises a pulse amplitude and the second therapy parameter comprises a pulse width. Example 24: the computer-readable storage medium of example 22, wherein the first therapy parameter comprises a pulse width and the second therapy parameter comprises a pulse amplitude.

Example 25: the computer-readable storage medium of any of examples 22-24, wherein the instructions that cause the one or more processors to adjust the present value of the second therapy parameter from the first value of the second therapy parameter to the second value for the second therapy parameter comprise instructions that cause the one or more processors to determine a scaling factor by which to decrease the first value of the second therapy parameter to the second value for the first therapy parameter, and wherein the instructions that cause the one or more processors to adjust the present value of the first therapy parameter from the first value of the first therapy parameter to the second value of the first therapy parameter comprise instructions that cause the one or more processors to increase the first value of the first therapy parameter to the second value of the first therapy parameter based on the determined scaling factor.

Example 26: the computer-readable storage medium of example 25, wherein the instructions that cause the one or more processors to decrease the first value of the second therapy parameter to the second value of the second therapy parameter based on the determined scaling factor comprise instructions that cause the one or more processors to multiply the first value of the second therapy parameter by an inverse of the scaling factor.

Example 27: the computer-readable storage medium of any of examples 22-26, wherein the second intensity is equal to an area-under-the-curve of a stimulation waveform defined by the second value for the first therapy parameter and the second value for the second therapy parameter, and wherein the first intensity is equal to an area-under-the-curve of a stimulation waveform defined by the first value of the first therapy parameter and the first value for the second therapy parameter.

Example 28: the computer-readable storage medium of any of examples 22-27, wherein the instructions that cause the one or more processors to, responsive to each of a plurality of user input entries to increase electrical stimulation therapy intensity, hold a value of a first therapy parameter substantially constant and increase a value of a second therapy parameter comprise instructions that cause the one or more processors to: determine a value of the increased electrical stimulation therapy intensity; determine a scaling factor to apply to the value of the second therapy parameter to increase the value of the second therapy parameter based on the value of the increased electrical stimulation therapy intensity; determine that the increased value of the second therapy parameter is less than or equal to the threshold value for the second therapy parameter; and increase the value of the second therapy parameter based on the determination that the increased value of the second therapy parameter is less than or equal to the threshold value for the second therapy parameter.

Example 29: the computer-readable storage medium of any of examples 22-28, further comprising instructions that cause the one or more processors to: determine that increasing the value of the second therapy parameter from the present value results in increasing the value of the second therapy parameter to be greater than the threshold value for the second therapy parameter.

Example 30: the computer-readable storage medium of example 29, wherein the instructions that cause the one or more processors to determine that increasing the value of the second therapy parameter from the present value results in increasing the value of the second therapy parameter to be greater than the threshold value for the second therapy parameter comprise instructions that cause the one or more processors to: determine an initial value for the second therapy parameter such that the initial value for the second therapy parameter and the value for the first therapy parameter result in electrical simulation therapy intensity equal to the value of the increased electrical stimulation therapy intensity; and determine that the initial value for the second therapy parameter is greater than the threshold value for the second therapy parameter to determine that increasing the value of the second therapy parameter from the present value results in increasing the value of the second therapy parameter to be greater than the threshold value for the second therapy parameter.

Example 31: the computer-readable storage medium of any of examples 22-30, further comprising instructions that cause the one or more processors to: select a first cathode electrode and a first anode electrode, wherein the instructions that cause the one or more processors to cause delivery of therapy at the second intensity comprise instructions that cause the one or more processors to cause delivery of therapy at the second intensity utilizing the first cathode electrode and the first anode electrode, the computer-readable storage medium further comprising instructions that cause the one or more processors to: based on a determination that the present value of the first therapy parameter and the second therapy parameter are at respective thresholds, select a second cathode electrode and a second anode electrode; responsive to each of a plurality of user input entries to increase electrical stimulation therapy intensity subsequent to the selection of the second cathode and the second anode electrode, hold the value of a first therapy parameter substantially constant and increase a value of a second therapy parameter; and cause delivery of therapy based on the first therapy parameter and the increased value of the second therapy parameter.

Example 32: a system comprising: means for holding a value of a first therapy parameter substantially constant and increasing a value of a second therapy parameter, responsive to each of a plurality of user input entries to increase electrical stimulation therapy intensity; means for adjusting the present value of the second therapy parameter from a first value of the second therapy parameter to a second value of the second therapy parameter, and adjusting a present value of the first therapy parameter from a first value of the first therapy parameter to a second value of the first therapy parameter, responsive to receiving a user input entry to increase electrical stimulation therapy intensity that causes a present value of the second therapy parameter to be at or greater than a threshold value for the second therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity; and means for causing delivery of therapy at the second intensity.

Example 33: The system of example 32 further comprising means for performing the method of any of examples 2-10.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
responsive to each of a plurality of user input entries to increase electrical stimulation therapy intensity, holding a value of a first therapy parameter substantially constant and increasing a value of a second therapy parameter;
responsive to receiving a user input entry to increase electrical stimulation therapy intensity that causes a present value of the second therapy parameter to be at or greater than a threshold value for the second therapy parameter, adjusting the present value of the second therapy parameter from a first value of the second therapy parameter to a second value of the second therapy parameter, and adjusting a present value of the first therapy parameter from a first value of the first therapy parameter to a second value of the first therapy parameter, wherein the second value of the first therapy parameter is greater than the first value of the first therapy parameter, wherein the second value of the second therapy parameter is less than the first value of the second therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity; and causing delivery of therapy at the second intensity.

2. The method of claim 1, wherein the first therapy parameter comprises a pulse amplitude and the second therapy parameter comprises a pulse width.

3. The method of claim 1, wherein the first therapy parameter comprises a pulse width and the second therapy parameter comprises a pulse amplitude.

4. The method of claim 1, wherein adjusting the present value of the second therapy parameter from the first value of the second therapy parameter to the second value for the second therapy parameter comprises determining a scaling factor by which to decrease the first value of the second therapy parameter to the second value for the first therapy parameter, and wherein adjusting the present value of the first therapy parameter from the first value of the first therapy parameter to the second value of the first therapy parameter comprises increasing the first value of the first therapy parameter to the second value of the first therapy parameter based on the determined scaling factor such that the second intensity is greater than or equal to the first intensity.

5. The method of claim 4, wherein decreasing the first value of the second therapy parameter to the second value of the second therapy parameter based on the determined scaling factor comprises multiplying the first value of the second therapy parameter by an inverse of the scaling factor.

6. The method of claim 1, wherein the second intensity is equal to an area-under-the-curve of a stimulation waveform defined by the second value for the first therapy parameter and the second value for the second therapy parameter, and wherein the first intensity is equal to an area-under-the-curve of a stimulation waveform defined by the first value of the first therapy parameter and the first value for the second therapy parameter.

7. The method of claim 1, wherein responsive to each of a plurality of user input entries to increase electrical stimulation therapy intensity, holding a value of a first therapy parameter substantially constant and increasing a value of a second therapy parameter comprises:

determining a value of the increased electrical stimulation therapy intensity;

determining a scaling factor to apply to the value of the second therapy parameter to increase the value of the second therapy parameter based on the value of the increased electrical stimulation therapy intensity;

determining that the increased value of the second therapy parameter is less than or equal to the threshold value for the second therapy parameter; and increasing the value of the second therapy parameter based on the determination that the increased value of the second therapy parameter is less than or equal to the threshold value for the second therapy parameter.

8. The method of claim 1, further comprising:

determining that increasing the value of the second therapy parameter from the present value results in increasing the value of the second therapy parameter to be greater than the threshold value for the second therapy parameter.

9. The method of claim 8, wherein determining that increasing the value of the second therapy parameter from the present value results in increasing the value of the second therapy parameter to be greater than the threshold value for the second therapy parameter comprises:

determining an initial value for the second therapy parameter such that the initial value for the second therapy parameter and the value for the first therapy parameter result in electrical simulation therapy intensity equal to the value of the increased electrical stimulation therapy intensity; and determining that the initial value for the second therapy parameter is greater than the threshold value for the second therapy parameter to determine that increasing the value of the second therapy parameter from the present value results in increasing the value of the second therapy parameter to be greater than the threshold value for the second therapy parameter.

10. The method of claim 1, further comprising:

selecting a first cathode electrode and a first anode electrode, wherein causing delivery of therapy at the second intensity comprises causing delivery of therapy at the second intensity utilizing the first cathode electrode and the first anode electrode, the method further comprising:

based on a determination that the present value of the first therapy parameter and the second therapy parameter are at respective thresholds, selecting a second cathode electrode and a second anode electrode;

responsive to each of a plurality of user input entries to increase electrical stimulation therapy intensity subsequent to the selection of the second cathode and the second anode electrode, holding the value of a first therapy parameter substantially constant and increasing a value of a second therapy parameter; and causing delivery of therapy based on the first therapy parameter and the increased value of the second therapy parameter.

11. The method of claim 1, wherein holding the value of the first therapy parameter substantially constant and increasing the value of a second therapy parameter comprises holding the value of the first therapy parameter constant and increasing the value of the second therapy parameter.

12. A system comprising:

a memory configured to store one or more threshold values for one or more therapy parameters; and processing circuitry configured to:

responsive to each of a plurality of user input entries to increase electrical stimulation therapy intensity, hold a value of a first therapy parameter substantially constant and increase a value of a second therapy parameter;

responsive to receiving a user input entry to increase electrical stimulation therapy intensity that causes a present value of the second therapy parameter to be at or greater than a threshold value stored in memory for the second therapy parameter, adjust the present value of the second therapy parameter from a first value of the second therapy parameter to a second value of the second therapy parameter, and adjust a present value of the first therapy parameter from a first value of the first therapy parameter to a second value of the first therapy parameter, wherein the second value of the first therapy parameter is greater than the first value of the first therapy parameter, wherein the second value of the second therapy parameter is less than the first value of the second parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity; and cause delivery of therapy at the second intensity.

13. The system of claim 12, wherein the first therapy parameter comprises a pulse amplitude and the second therapy parameter comprises a pulse width.

14. The system of claim 12, wherein the first therapy parameter comprises a pulse width and the second therapy parameter comprises a pulse amplitude.

15. The system of claim 12, wherein to adjust the present value of the second therapy parameter from the first value of the second therapy parameter to the second value for the second therapy parameter, the processing circuitry is configured to determine a scaling factor by which to decrease the first value of the second therapy parameter to the second value for the first therapy parameter, and wherein to adjust the present value of the first therapy parameter from the first value of the first therapy parameter to the second value of the first therapy parameter, the processing circuitry is configured to increase the first value of the first therapy parameter to the second value of the first therapy parameter based on the determined scaling factor such that the second intensity is greater than or equal to the first intensity.

16. The system of claim 15, wherein to decrease the first value of the second therapy parameter to the second value of the second therapy parameter based on the determined scaling factor, the processing circuitry is configured to multiply the first value of the second therapy parameter by an inverse of the scaling factor.

17. The system of claim 12, wherein the second intensity is equal to an area-under-the-curve of a stimulation waveform defined by the second value for the first therapy parameter and the second value for the second therapy parameter, and wherein the first intensity is equal to an area-under-the-curve of a stimulation waveform defined by the first value of the first therapy parameter and the first value for the second therapy parameter.

18. The system of claim 12, wherein to hold a value of a first therapy parameter substantially constant and increase a value of a second therapy parameter responsive to each of a plurality of user input entries to increase electrical stimulation therapy intensity, the processing circuitry is configured to:
determine a value of the increased electrical stimulation therapy intensity;
determine a scaling factor to apply to the value of the second therapy parameter to increase the value of the second therapy parameter based on the value of the increased electrical stimulation therapy intensity;
determine that the increased value of the second therapy parameter is less than or equal to the threshold value for the second therapy parameter; and
increase the value of the second therapy parameter based on the determination that the increased value of the second therapy parameter is less than or equal to the threshold value for the second therapy parameter.

19. The system of claim 12, wherein the processing circuitry is configured to:
determine that increasing the value of the second therapy parameter from the present value results in increasing the value of the second therapy parameter to be greater than the threshold value for the second therapy parameter.

20. The system of claim 19, wherein to determine that increasing the value of the second therapy parameter from the present value results in increasing the value of the second therapy parameter to be greater than the threshold value for the second therapy parameter, the processing circuitry is configured to:
determine an initial value for the second therapy parameter such that the initial value for the second therapy parameter and the value for the first therapy parameter result in electrical simulation therapy intensity equal to the value of the increased electrical stimulation therapy intensity; and
determine that the initial value for the second therapy parameter is greater than the threshold value for the second therapy parameter to determine that increasing the value of the second therapy parameter from the present value results in increasing the value of the second therapy parameter to be greater than the threshold value for the second therapy parameter.

21. The system of claim 12, wherein the processing circuitry is configured to select a first cathode electrode and a first anode electrode, wherein to cause delivery of therapy at the second intensity, the processing circuitry is configured to cause delivery of therapy at the second intensity utilizing the first cathode electrode and the first anode electrode, and wherein the processing circuitry is further configured to:
based on a determination that the present value of the first therapy parameter and the second therapy parameter are at respective thresholds, select a second cathode electrode and a second anode electrode;
responsive to each of a plurality of user input entries to increase electrical stimulation therapy intensity subsequent to the selection of the second cathode and the second anode electrode, hold the value of a first therapy parameter substantially constant and increasing a value of a second therapy parameter; and
cause delivery of therapy based on the first therapy parameter and the increased value of the second therapy parameter.

22. The system of claim 12, further comprising an implantable medical device (IMD), wherein the IMD comprises the memory and the processing circuitry.

23. The system of claim 12, wherein to hold the value of the first therapy parameter substantially constant and increase the value of a second therapy parameter, the processing circuitry is configured to hold the value of the first therapy parameter constant and increase the value of the second therapy parameter.

24. A computer-readable storage medium comprising instructions to cause a programmable processor to:
responsive to each of a plurality of user input entries to increase electrical stimulation therapy intensity, hold a value of a first therapy parameter substantially constant and increasing a value of a second therapy parameter;
responsive to receiving a user input entry to increase electrical stimulation therapy intensity that causes a present value of the second therapy parameter to be at or greater than a threshold value for the second therapy parameter, adjust the present value of the second therapy parameter from a first value of the second therapy parameter to a second value of the second therapy parameter, and adjust a present value of the first therapy parameter from a first value of the first therapy parameter to a second value of the first therapy parameter, wherein the second value of the first therapy parameter is greater than the first value of the first therapy parameter, wherein the second value of the second therapy parameter is less than the first value of the second therapy parameter, wherein the first value of the first therapy parameter and the first value of the second therapy parameter set a first intensity and the second value of the first therapy parameter and the second value of the second therapy parameter set a second intensity, and wherein the second intensity is greater than or equal to the first intensity; and cause delivery of therapy at the second intensity.

25. The computer-readable storage medium of claim 24, wherein the first therapy parameter comprises a pulse amplitude and the second therapy parameter comprises a pulse width.

26. The computer-readable storage medium of claim 24, wherein the first therapy parameter comprises a pulse width and the second therapy parameter comprises a pulse amplitude.

27. The computer-readable storage medium of claim 24, wherein the instructions that cause the one or more processors to adjust the present value of the second therapy parameter from the first value of the second therapy parameter to the second value for the second therapy parameter comprise instructions that cause the one or more processors to determine a scaling factor by which to decrease the first value of the second therapy parameter to the second value for the first therapy parameter, and wherein the instructions that cause the one or more processors to adjust the present value of the first therapy parameter from the first value of the first therapy parameter to the second value of the first therapy parameter comprise instructions that cause the one or more processors to increase the first value of the first therapy parameter to the second value of the first therapy parameter based on the determined scaling factor such that the second intensity is greater than or equal to the first intensity.

28. The computer-readable storage medium of claim 27, wherein the instructions that cause the one or more processors to decrease the first value of the second therapy parameter to the second value of the second therapy parameter based on the determined scaling factor comprise instructions that cause the one or more processors to multiply the first value of the second therapy parameter by an inverse of the scaling factor.

29. The computer-readable storage medium of claim 24, wherein the second intensity is equal to an area-under-the-curve of a stimulation waveform defined by the second value for the first therapy parameter and the second value for the second therapy parameter, and wherein the first intensity is equal to an area-under-the-curve of a stimulation waveform defined by the first value of the first therapy parameter and the first value for the second therapy parameter.

30. The computer-readable storage medium of claim 24, wherein the instructions that cause the one or more processors to, responsive to each of a plurality of user input entries to increase electrical stimulation therapy intensity, hold a value of a first therapy parameter substantially constant and increase a value of a second therapy parameter comprise instructions that cause the one or more processors to:

determine a value of the increased electrical stimulation therapy intensity;

determine a scaling factor to apply to the value of the second therapy parameter to increase the value of the second therapy parameter based on the value of the increased electrical stimulation therapy intensity;

determine that the increased value of the second therapy parameter is less than or equal to the threshold value for the second therapy parameter; and increase the value of the second therapy parameter based on the determination that the increased value of the second therapy parameter is less than or equal to the threshold value for the second therapy parameter.

31. The computer-readable storage medium of claim 24, further comprising instructions that cause the one or more processors to:

determine that increasing the value of the second therapy parameter from the present value results in increasing the value of the second therapy parameter to be greater than the threshold value for the second therapy parameter.

32. The computer-readable storage medium of claim 31, wherein the instructions that cause the one or more processors to determine that increasing the value of the second therapy parameter from the present value results in increasing the value of the second therapy parameter to be greater than the threshold value for the second therapy parameter comprise instructions that cause the one or more processors to:

determine an initial value for the second therapy parameter such that the initial value for the second therapy parameter and the value for the first therapy parameter result in electrical simulation therapy intensity equal to the value of the increased electrical stimulation therapy intensity; and determine that the initial value for the second therapy parameter is greater than the threshold value for the second therapy parameter to determine that increasing the value of the second therapy parameter from the present value results in increasing the value of the second therapy parameter to be greater than the threshold value for the second therapy parameter.

33. The computer-readable storage medium of claim 24, further comprising instructions that cause the one or more processors to:

select a first cathode electrode and a first anode electrode, wherein the instructions that cause the one or more processors to cause delivery of therapy at the second intensity comprise instructions that cause the one or more processors to cause delivery of therapy at the second intensity utilizing the first cathode electrode and the first anode electrode based on 300 micro-seconds pulse width and 800 Hz frequency, the computer-readable storage medium further comprising instructions that cause the one or more processors to:

based on a determination that the present value of the first therapy parameter and the second therapy parameter are at respective thresholds, select a second cathode electrode and a second anode electrode;

responsive to each of a plurality of user input entries to increase electrical stimulation therapy intensity subsequent to the selection of the second cathode and the second anode electrode, hold the value of a first therapy parameter substantially constant and increase a value of a second therapy parameter; and cause delivery of therapy based on the first therapy parameter and the increased value of the second therapy parameter.

34. The computer-readable storage medium of claim 24, wherein the instructions that cause the one or more processors to hold the value of the first therapy parameter substantially constant and increase the value of a second therapy parameter comprise instructions that cause the one or more processors to hold the value of the first therapy parameter constant and increase the value of the second therapy parameter.

* * * * *